United States Patent
Ashkenazi et al.

(10) Patent No.: US 11,452,276 B2
(45) Date of Patent: Sep. 27, 2022

(54) **TOLERANCE IN PLANTS OF *SOLANUM LYCOPERSICUM* TO THE TOBAMOVIRUS TOMATO BROWN RUGOSE FRUIT VIRUS (TBRFV)**

(71) Applicant: VILMORIN & CIE, Paris (FR)

(72) Inventors: Varda Ashkenazi, Berurim (IL); Yaniv Rotem, Berurim (IL); Ron Ecker, Berurim (IL); Shai Nashilevitz, Berurim (IL); Naama Barom, Berurim (IL)

(73) Assignee: VILMORIN & CIE, Paris (FR)

( * ) Notice: Subject to any disclaimer, the term of this patent is extended or adjusted under 35 U.S.C. 154(b) by 15 days.

(21) Appl. No.: 16/616,825

(22) PCT Filed: May 29, 2018

(86) PCT No.: PCT/EP2018/064055
§ 371 (c)(1),
(2) Date: Nov. 25, 2019

(87) PCT Pub. No.: WO2018/219941
PCT Pub. Date: Dec. 6, 2018

(65) Prior Publication Data
US 2021/0171975 A1 Jun. 10, 2021

(30) Foreign Application Priority Data

Jun. 1, 2017 (EP) ..................... 17305644

(51) Int. Cl.
*A01H 6/82* (2018.01)
*C12N 15/82* (2006.01)
*A01H 5/08* (2018.01)
*C12Q 1/6895* (2018.01)

(52) U.S. Cl.
CPC .............. *A01H 6/825* (2018.05); *A01H 5/08* (2013.01); *C12N 15/8283* (2013.01); *C12Q 1/6895* (2013.01); *C12Q 2600/13* (2013.01)

(58) Field of Classification Search
None
See application file for complete search history.

(56) References Cited

U.S. PATENT DOCUMENTS

2016/0242376 A1    8/2016   Jiang

FOREIGN PATENT DOCUMENTS

| WO | WO 2013/064641 A1 | 5/2013 |
| WO | WO 2017/012951 A1 | 1/2017 |
| WO | WO 2019/110130 A1 | 6/2019 |

OTHER PUBLICATIONS

Johnson et al (2012 Genes Genomes Genetics 2:1145-1159 (Year: 2012).*
Ainong Shi et al., "Molecular Markers for Tm-2 Alleles of Tomato Mosaic Virus Resistance in Tomato", American Journal of Plant Sciences, vol. 2, No. 2, Jan. 1, 2011, pp. 180-189.
P. Kadirvel et al., "Mapping of QTLs in tomato line FLA456 associated with resistance to a virus causing tomato yellow leaf curl disease", Euphytica, vol. 190, No. 2, Dec. 5, 2012, pp. 297-308.
Salem N. et al, "A new tobamovirus infecting tomato crops in Jordan", Archives of Virology, Springer Wien, AT, vol. 161, No. 2, Nov. 19, 2015, pp. 503-506.
Wojciech Szczechura et al., "Tomato Molecular Markers", Vegetable Crops Research Bulletin, vol. 74, Jun. 13, 2011, pp. 5-23.
International Search Report dated Jul. 27, 2018 in connection with PCT International Application No. PCT/EP2018/064055.
Written Opinion (form PCT/TSA/237) dated Jul. 27, 2018 in connection with PCT International Application No. PCT/EP2018/064055.
Bombarely A. et al., "The sol genomics network (solgenomics.net): growing tomatoes using Perl", Nucleic Acids Research, 2011, vol. 39, D1149-D1155.
Li J. et al., "Seedling salt tolerance in tomato", Euphytica (2011) 178: 403-414.
Seift A. et al., "Genetics and molecular mechanisms of resistance to powdery mildews in tomato (*Solanum lycopersicum*) and its wild relatives", Eur J Plant Pathol (2014) 138: 641-665.

* cited by examiner

*Primary Examiner* — Brent T Page
(74) *Attorney, Agent, or Firm* — John P. White

(57) ABSTRACT

The invention relates to a *Solanum lycopersicum* plant comprising in its genome QTLs confering to the plant an improved phenotype corresponding to foliar and/or fruit tolerance and/or resistance to Tomato Brown Rugose Fruit virus, with respect to a corresponding plant devoid of said QTLs, and wherein said QTLs are chosen from those present in the genome of a plant of the seeds HAZTBRFVRES1 NCIMB accession number 42758. The QTL are preferably characterized by defined alleles of different SNPs on chromosome 6, 9 and 11. The invention is also directed to parts of these plants with improved phenotype, as well as progeny, to the use of these plants for introgressing the improved phenotype in another genetic background, as well as to different methods for obtaining tomato plants or seeds with increased foliar and/or fruit tolerance or resistance to Tomato Brown Rugose Fruit virus.

16 Claims, 3 Drawing Sheets

Figure 1:
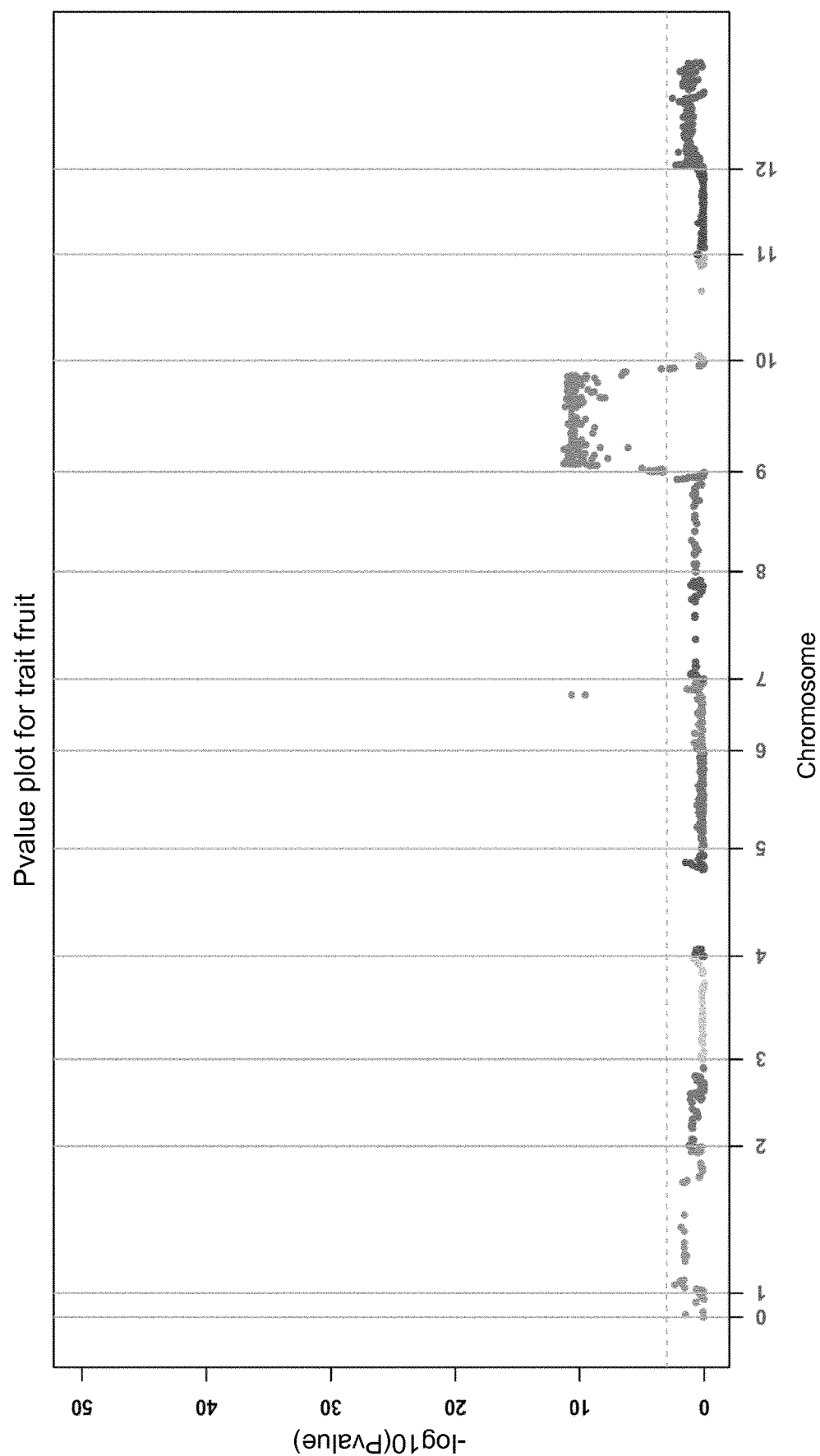

Specification includes a Sequence Listing.

TOLERANCE IN PLANTS OF *SOLANUM LYCOPERSICUM* TO THE TOBAMOVIRUS TOMATO BROWN RUGOSE FRUIT VIRUS (TBRFV)

The present invention relates to tolerance or resistance in plants of *Solanum lycopersicum*, also known as *Lycopersicum esculentum*, to the tobamovirus Tomato Brown Rugose Fruit virus (TBRFV). More specifically, the present invention relates to tomato plants and fruits comprising one or more genetic determinants that leads to tolerance or resistance to the Tomato Brown Rugose Fruit virus. The invention further relates to markers linked to the one or more genetic determinant(s) and to the use of such makers to identify or select the genetic determinant(s) and to identify or select plants carrying such tolerance or resistance. The invention also relates to the seeds and progeny of such plants and to propagation material for obtaining such plants, and to different uses of these plants.

BACKGROUND OF THE INVENTION

All cultivated and commercial forms of tomato belong to a species most frequently referred to as *Lycopersicon esculentum Miller*. *Lycopersicon* is a relatively small genus within the extremely large and diverse family Solanaceae which is considered to consist of around 90 genera, including pepper, tobacco and eggplant. The genus *Lycopersicon* has been divided into two subgenera, the *esculentum* complex which contains those species that can easily be crossed with the commercial tomato and the *peruvianum* complex which contains those species which are crossed with considerable difficulty (Stevens, M., and Rick, C. M. 1986). Due to its value as a crop, *L. esculentum Miller* has become widely disseminated all over the world. Even if the precise origin of the cultivated tomato is still somewhat unclear, it seems to come from the Americas, being native to Ecuador, Peru and the Galapagos Island and initially cultivated by Aztecs and Incas as early as 700 AD. Mexico appears to have been the site of domestication and the source of the earliest introduction. It is supposed that the cherry tomato, *L. esculentum* var. *cerasiforme*, is the direct ancestor of modern cultivated forms.

Tomato is grown for its fruit, widely used as a fresh market or processed product. As a crop, tomato is grown commercially wherever environmental conditions permit the production of an economically viable yield. The majority of fresh market tomatoes are harvested by hand at vine ripe and mature green stage of ripeness. Fresh market tomatoes are available year round. Processing tomato are mostly mechanically harvested and used in many forms, as canned tomatoes, tomato juice, tomato sauce, puree, paste or even catsup.

Tomato is a normally simple diploid species with twelve pairs of differentiated chromosomes. However, polyploidy tomato is also part of the present invention. The cultivated tomato is self-fertile and almost exclusively self-pollinating. The tomato flowers are hermaphrodites. Commercial cultivars were initially open pollinated. As hybrid vigor has been identified in tomatoes, hybrids are replacing the open pollinated varieties by gaining more and more popularity amongst farmers with better yield and uniformity of plant characteristics. Due to its wide dissemination and high value, tomato has been intensively bred. This explains why such a wide array of tomato is now available. The shape may range from small to large, and there are cherry, plum, pear, blocky, round, and beefsteak types.

Tomatoes may be grouped by the amount of time it takes for the plants to mature fruit for harvest and, in general the cultivars are considered to be early, midseason or late-maturing. Tomatoes can also be grouped by the plant's growth habit; determinate, semi-determinate or indeterminate. Determinate plants tend to grow their foliage first, then set flowers that mature into fruit if pollination is successful. All of the fruits tend to ripen on a plant at about the same time. Indeterminate tomatoes start out by growing some foliage, then continue to produce foliage and flowers throughout the growing season. These plants will tend to have tomato fruit in different stages of maturity at any given time. The semi-determinate tomatoes have a phenotype between determinate and indeterminate, they are typical determinate types except that grow larger than determinate varieties. More recent developments in tomato breeding have led to a wider array of fruit color. In addition to the standard red ripe color, tomatoes can be creamy white, lime green, pink, yellow, golden, orange or purple.

Hybrid commercial tomato seed can be produced by hand pollination. Pollen of the male parent is harvested and manually applied to the stigmatic surface of the female inbred. Prior to and after hand pollination, flowers are covered so that insects do not bring foreign pollen and create a mix or impurity. Flowers are tagged to identify pollinated fruit from which seed will be harvested.

A variety of pathogens affect the productivity of tomato plants, including virus, fungi, bacteria, nematodes and insects. Tomatoes are inter alia susceptible to many viruses and virus resistance is therefore of major agricultural importance.

Tobamoviruses are among the most important plant viruses causing severe damages in agriculture, especially to vegetable and ornamental crops around the world. Tobamoviruses are easily transmitted by mechanical means, as well as through seed transmission. Tobamoviruses are generally characterized by a rod-shaped particle of about 300nm encapsidating a single stranded, positive RNA genome encoding four proteins. In tomatoes, tobacco mosaic virus (TMV), tomato mosaic virus (ToMV) are feared by growers worldwide as they can severely damage crop production, for example through irregular ripening (fruits having yellowish patches on the surface and brownish spots beneath the surface). Several genes have however been identified by plants breeders over the years and TMV and/or ToMV resistant tomato varieties are nowadays available.

In recent years, a severe outbreak of virus affected tomato productions areas in the middle east, such as in Jordan and in Israel. Most of the tomato varieties affected were considered TMV and/or ToMV resistant, but were still severely affected and showed typical TMV/ToMV like symptoms: while the foliar ones were quite similar to the TMV/ToMV symptoms, the fruit symptoms were much more frequent and severe than the usual symptoms from such viruses with fruits lesions and deformations. The fruit quality was very poor and rather unmarketable. Salem et al (Arch.Virol. 161 (2), 503-506. 35 2015) extracted RNA from fruit and leaves of symptomatic plants and made various tests leading to the identification of a new Tobamovirus species that they proposed to name Tomato Brown Rugose Fruit virus (TBRFV). The resistance to TMV and/or ToMV does not confer resistance to this new virus TBRFV.

As Tobamoviruses are not easily controlled but through genetic improvement by the identification and use in breeding of resistance genes, and as the resistance genes currently available to control TMV and/or ToMV are useless against the damages from the new Tomato Brown Rugose Fruit virus, there is an urgent need to identify resistance and/or tolerance against this new Tobamovirus, failing that would result in entire regions in which tomato crop could not be produced anymore.

SUMMARY

The present inventors have identified tomato plants which display a tolerance or resistance to the Tomato Brown Rugose Fruit virus and they have been able to localize and identify genetic determinants, also referred hereafter as QTLs (Quantitative Trait Locus) that lead to tolerance or resistance to the Tomato Brown Rugose Fruit virus.

The tolerance or resistance according to the present invention is imparted by the newly discovered genetic determinants that can confer a tolerance or resistance to the Tomato Brown Rugose Fruit virus (TBRFV) at the level of the leaves of the tomato plants infected by the virus, at the level of the fruits of the tomato plants infected by the virus or at the level of both leaves and fruits. The newly discovered genetic determinants have a recessive nature. As the fruit tolerance and/or resistance is imparted independently by two QTLs and the foliar resistance by one QTL, their transfer to different genetic background, i.e. into various tomatoes can be easily carried out by a skilled artisan in plant breeding, especially given the information regarding suitable markers associated with the QTLs provided by the inventors.

The present invention thus provides these genetic determinants, also here named QTLs, conferring, when present in the homozygous state, the phenotype of TBRFV tolerance or resistance at the level of the tomato leaves and/or fruits of the tomato plants infected by the TBRFV.

The present invention provides commercial *S. lycopersicum* plants that display tolerance or resistance to TBRFV as well as methods that produce or identify *S. lycopersicum* plants or populations (germplasm) that display resistance to TBRFV. The present invention also discloses molecular genetic markers, especially SNPs, linked to the QTLs that lead to tolerance or resistance to the TBRFV, which can be leaves and/or fruit tolerance or resistance and that are of a recessive nature. Plants obtained through the methods and uses of such molecular markers are also provided. The invention also provides several methods and uses of the information linked to these SNPs associated to the QTL conferring the TBRFV tolerance, inter alia methods for identifying TBRFV tolerant plants and methods for identifying further molecular markers linked to this tolerance, as well as methods for improving the yield of tomato production in an environment infested by TBRFV and methods for protecting a tomato field from TBRFV infestation.

Definitions:

The term "Resistance" is as defined by the ISF (International Seed Federation) Vegetable and Ornamental Crops Section for describing the reaction of plants to pests or pathogens, and abiotic stresses for the Vegetable Seed Industry. Specifically, by resistance, it is meant the ability of a plant variety to restrict the growth and development of a specified pest or pathogen and/or the damage they cause when compared to susceptible plant varieties under similar environmental conditions and pest or pathogen pressure. Resistant varieties may exhibit some disease symptoms or damage under heavy pest or pathogen pressure.

The term 'Tolerance' is used herein to indicate a phenotype of a plant wherein at least some of the disease-symptoms remain absent upon exposure of said plant to an infective dose of virus, whereby the presence of a systemic or local infection, virus multiplication, at least the presence of viral genomic sequences in cells of said plant and/or genomic integration thereof can be established, at least under some culture conditions. Tolerant plants are therefore resistant for symptom expression but symptomless carriers of the virus. Sometimes, viral sequences may be present or even multiply in plants without causing disease symptoms. It is to be understood that a tolerant plant, although it is infected by the virus, is generally able to restrict at least moderately the growth and development of the virus. Moreover, some plants may be tolerant under some culture conditions, and resistant under different conditions. Tolerance and Resistance are thus not mutually exclusive.

In case of TBRFV, by leave tolerance, or foliar tolerance, it is meant the phenotype of a plant wherein the disease symptoms on the leaves remain absent upon exposure of said plant to an infective dose of TBRFV. Disease symptoms on the fruits may however be present on infected plants.

By fruit tolerance, in case of TBRFV, it is meant the phenotype of a plant wherein the disease symptoms on the fruits remain absent upon exposure of said plant to an infective dose of TBRFV. Disease symptoms on the leaves may however be present on infected plants.

Symptoms on leaves of TBRFV infection generally include mosaic, distortion of the leaflets and in many cases also shoestrings like symptoms. Symptoms on fruits of TBRFV infection generally include typical yellow lesions and deformation of the fruits. In many cases there are also "chocolate spots" on the fruits.

Susceptibility: The inability of a plant variety to restrict the growth and development of a specified pest or pathogen; a susceptible plant displays the detrimental symptoms linked to the virus infection, namely the foliar damages and fruit damages in case of TBRFV infection.

A *S. lycopersicum* plant susceptible to Tomato Brown Rugose Fruit virus, is for example the commercially available variety Candela as mentioned in the 2015 Salem et al. publication. It can also be the Hazera No 2 and Hazera No 4 lines mentioned in the example part of the present application. All commercially available varieties of tomato grown in TBRFV infected area are, to date, i.e. before the present invention, susceptible to TBRFV.

A plant according to the invention has thus at least improved resistance or tolerance to Tomato Brown Rugose Fruit virus, more specifically at least improved foliar tolerance or fruit tolerance to TBRFV, with respect to the variety Candela, and more generally with respect to any commercial variety of tomato grown in Tomato Brown Rugose Fruit virus infected area.

As used herein, the term "offspring" or "progeny" refers to any plant resulting as progeny from a vegetative or sexual reproduction from one or more parent plants or descendants thereof. For instance an offspring plant may be obtained by cloning or selfing of a parent plant or by crossing two parents plants and include selfings as well as the F1 or F2 or still further generations. An F1 is a first-generation offspring produced from parents at least one of which is used for the first time as donor of a trait, while offspring of second generation (F2) or subsequent generations (F3, F4, etc.) are specimens produced from selfings of F1's, F2's etc. An F1 may thus be (and usually is) a hybrid resulting from a cross between two true breeding parents (true-breeding is homozygous for a trait), while an F2 may be (and usually is) an offspring resulting from self-pollination of said F1 hybrids. As used herein, the term "cross", "crossing", "cross pollination" or "cross-breeding" refer to the process by which the pollen of one flower on one plant is applied (artificially or naturally) to the ovule (stigma) of a flower on another plant.

As used herein, the term "genetic determinant" and/or "QTL" refers to any segment of DNA associated with a biological function. Thus, QTLs and/or genetic determinants include, but are not limited to, genes, coding sequences and/or the regulatory sequences required for their expression. QTLs and/or genetic determinants can also include nonexpressed DNA segments that, for example, form recognition sequences for other proteins.

As used herein, the term "genotype" refers to the genetic makeup of an individual cell, cell culture, tissue, organism (e.g., a plant), or group of organisms.

As used herein, the term "grafting" is the operation by which a rootstock is grafted with a scion. The primary motive for grafting is to avoid damages by soil-born pest and pathogens when genetic or chemical approaches for disease management are not available. Grafting a susceptible scion onto a resistant rootstock can provide a resistant cultivar without the need to breed the resistance into the cultivar. In addition, grafting may enhance tolerance to abiotic stress, increase yield and result in more efficient water and nutrient uses.

As used herein, the term "heterozygote" refers to a diploid or polyploid individual cell or plant having different alleles (forms of a given gene, genetic determinant or sequences) present at least at one locus.

As used herein, the term "heterozygous" refers to the presence of different alleles (forms of a given gene, genetic determinant or sequences) at a particular locus.

As used herein, "homologous chromosomes", or "homologs" (or homologues), refer to a set of one maternal and one paternal chromosomes that pair up with each other during meiosis. These copies have the same genes in the same loci and the same centromere location.

As used herein, the term "homozygote" refers to an individual cell or plant having the same alleles at one or more loci on all homologous chromosomes.

As used herein, the term "homozygous" refers to the presence of identical alleles at one or more loci in homologous chromosomal segments.

As used herein, the term "hybrid" refers to any individual cell, tissue or plant resulting from a cross between parents that differ in one or more genes.

As used herein, the term "locus" (plural: "loci") refers to any site that has been defined genetically, this can be a single position (nucleotide) or a chromosomal region. A locus may be a gene, a genetic determinant, or part of a gene, or a DNA sequence, and may be occupied by different sequences. A locus may also be defined by a SNP (Single Nucleotide Polymorphism), by several SNPs, or by two flanking SNPs.

As used herein, the term "rootstock" is the lower part of a plant capable of receiving a scion in a grafting process.

As used herein, the term "scion" is the higher part of a plant capable of being grafted onto a rootstock in a grafting process.

DETAILED DESCRIPTION OF THE INVENTION

The present inventors have identified three QTLs which, when present homozygously into a *S. lycopersicum* plant, alone or in combination such as the combinations described elsewhere in the application, provide an improved tolerance and/or resistance in the fruits and/or leaves of a tomato plant infected or likely to be infected by the Tomato Brown Rugose Fruit virus (TBRFV).

The present inventors have identified two QTLs, namely QTL1 and QTL2, which when present homozygously into a *S. lycopersicum* background, especially on chromosomes 6 and 9, confer independently or in combination an improved tolerance in the fruits of a tomato plant infected or likely to be infected by the TBRFV. Further, the present inventors have identified one QTL, which, when present homozygously into a *S. lycopersicum* background, especially on chromosome 11, confers an improved tolerance in the leaves of a tomato plant infected or likely to be infected by the TBRFV. When present homozygously on chromosomes 6, 9 and 11, the three QTLs confers improved tolerance and/or resistance in both leaves and fruits of a tomato plant infected or likely to be infected by the TBRFV.

As demonstrated in the examples, the phenotype of the plants according to the invention is, in most circumstances, best characterized as tolerance rather than resistance to TBRFV, namely foliar tolerance, fruit tolerance or both forms of tolerance; under specific circumstances, the plants of the invention however exhibit resistance to TBRFV. In the following, reference is made to tolerance to TBRFV; this phenotype however encompasses resistance phenotype, under specific circumstances.

According to a first aspect, the invention is thus directed to a *S. lycopersicum* plant comprising in its genome one or two QTLs, namely QTL1 and/or QTL2, which when present homozygously into a *S. lycopersicum* background, especially on chromosomes 6 and/or 9 respectively, confer independently an improved tolerance in the fruits of a tomato plant infected by the Tomato Brown Rugose Fruit virus. QTL1 is located on chromosome 6 and QTL 2 is located on chromosome 9. The invention is thus directed to a *S. lycopersicum* plant comprising in its genome a QTL, namely QTL1 which when present homozygously into a *S. lycopersicum* background, especially on chromosome 6, confer an improved tolerance in the fruits of a tomato plant to TBRFV infection. The invention is also directed to a *S. lycopersicum* plant comprising in its genome a QTL, namely QTL2 which when present homozygously into a *S. lycopersicum* background, especially on chromosome 9, confer an improved tolerance in the fruits of a tomato plant to TBRFV infection.

According to an embodiment, the invention is further directed to a *S. lycopersicum* plant comprising in its genome one QTL, namely QTL3, which, when present homozygously into a *S. lycopersicum* background, especially on chromosome 11, confers an improved tolerance in the leaves of a tomato plant infected by the Tomato Brown Rugose Fruit virus.

The invention is more specifically directed to plants comprising homozygously in their genome QTL1 on chromosome 6, or QTL2 on chromosome 9, or both QTLs, which independently confer fruit tolerance to TBRFV. The invention is also directed to plants comprising homozygously in their genome QTL3 on chromosome 11 conferring foliar tolerance to TBRFV.

According to an embodiment, the invention is directed to a *S. lycopersicum* plant comprising in its genome various combinations of QTL1, QTL2 and QTL3 which when present homozygously into a *S. lycopersicum* background, confer an improved tolerance and/or resistance in the fruits and leaves of a tomato plant infected by the Tomato Brown Rugose Fruit virus. Such combinations could be QTL1 and QTL3, QTL2 and QTL3, QTL1, QTL2 and QTL3. More preferably, such a combination is QTL1, QTL2 and QTL3. All the QTLs are preferably present homozygously.

The invention is also directed to a cell of such plants from previous aspects, as well as seeds comprising said QTLs.

The QTLs according to the invention and conferring the improved tolerance to TBRFV are chosen from the ones present in the genome of seeds of HAZTBRFVRES1. A sample of this *S. lycopersicum* seed has been deposited by Hazera Seeds Ltd. Berurim, M.P. Shimim 79837, Israel, pursuant to and in satisfaction of the requirements of the Budapest treaty on the International Recognition of the deposit of Microorganisms for the Purpose of Patent procedure ("the Budapest Treaty" with the National collection of Industrial, Food and Marine bacteria (NCIMB) (NCIMB, Ltd, Ferguson Building, Craibstone Estate, Bucksburn, Aberdeen AB21 9YA, united Kingdom) on 16 May 2017 under accession number 42758. A deposit of this tomato seed is maintained by Hazera Seeds Ltd. Berurim, M.P. Shimim 79837, Israel.

The QTLs conferring the improved tolerance to TBRFV are preferably located on chromosome 6 for QTL1, on chromosome 9 for QTL2 and on chromosome 11 for QTL3. They are more preferably located within a chromosomal interval of chromosome 6 which comprises the SNP TO-0005197 (SEQ ID NO:1) and the SNP TO-0145581 (SEQ ID NO:2) for QTL1, within a chromosomal interval of chromosome 9 which comprises the SNP TO-0180955 (SEQ ID NO:3) and the SNP TO-0196109 (SEQ ID NO:6) for QTL2 and within a chromosomal interval of chromosome 11 which comprises the SNP TO-0122252 (SEQ ID NO:7) and the SNP TO-0162427(SEQ ID NO:18) for QTL3.

The specific polymorphisms corresponding to the SNPs (Single Nucleotide Polymorphism) referred to in this description, as well as the flanking sequences of these SNPs in the *S. lycopersicum* genome, are given in the experimental section (see inter alia tables 4, 5, 6, 7, 9 and 10) and the accompanying sequence listing. Their location with respect to the version 2.40 of the tomato genome, on chromosomes 6, 9 and 11, is indicated in tables 4, 6 and 9 and their flanking sequences are also illustrated in tables 5, 7 and 10, and in the sequence listing.

It is to be noted in this respect that, by definition, a SNP refers to a single nucleotide in the genome, which is variable depending on the allele which is present, whereas the flanking nucleotides are identical. For ease of clear identification of the position of the different SNPs, their position is given in tables 4, 6 and 9, by reference to the tomato genome sequence in its version 2.40 and by reference to their flanking sequences, identified by SEQ ID number. In the sequence associated with a specific SNP in the present application, for example SEQ ID No:1 for the SNP TO-0005197, only one nucleotide within the sequence actually corresponds to the polymorphism, namely the 61' nucleotide of SEQ ID No:1 corresponds to the polymorphic position of SNP TO-0005197, which can be T or C as indicated in tables 4, 5 and 6. The flanking sequences are given for positioning the SNP in the genome but are not part of the polymorphism as such.

The present inventors have identified that the QTLs responsible for the phenotype of interest, i.e. an improved tolerance in its leaves and/or fruits when infected by the TBRFV are to be found in the chromosomal regions mentioned above, by identifying the presence of sequences at different loci along said region, namely at 18 different loci defined by the 18 following SNPs: TO-0005197 (SEQ ID NO:1) and TO-0145581 (SEQ ID NO:2) for QTL1 on chromosome 6, TO-0180955 (SEQ ID NO:3), TO-0196724 (SEQ ID NO:4), TO-0145125 (SEQ ID NO:5) and TO-0196109 (SEQ ID NO:6) for QTL2 on chromosome 9 and TO-0122252 (SEQ ID NO:7), TO-0144317 (SEQ ID NO:8), TO-0142270 (SEQ ID NO:9), TO-0142294 (SEQ ID NO:10), TO-0142303 (SEQ ID NO:11), TO-0142306 (SEQ ID NO:12), TO-0182276 (SEQ ID NO:13), TO-0181040 (SEQ ID NO:14), TO-0123057 (SEQ ID NO:15), TO-0125528 (SEQ ID NO:16), TO-0162432 (SEQ ID NO:17) and TO-0162427 (SEQ ID NO:18) for QTL3 on chromosome 11.

A tomato plant according to the invention having an improved tolerance in its fruits when infected by the TBRFV has QTL imparting said phenotype at at least one of the loci on chromosome 6 and/or on chromosome 9. Preferably, a tomato plant according to the invention having an improved fruit tolerance when infected by the Tomato Brown Rugose Fruit virus has a QTL at at least one of the loci on chromosome 6 and at least one of the loci on chromosome 9. Alternatively, a tomato plant of the invention has a QTL imparting the fruit tolerance to TBRFV at at least one of the two loci on chromosome 6 detailed above; or has a QTL imparting the fruit tolerance to TBRFV at at least one of the four loci on chromosome 9 detailed above.

A tomato plant according to the invention having an improved tolerance in its leaves when infected by the TBRFV will have QTLs at at least one of the loci on chromosome 11.

A tomato plant according to the invention having an improved tolerance at the level of both its leaves and fruits when infected by the Tomato Brown Rugose Fruit virus will have sequences conferring the phenotype at at least one of the loci on chromosome 6 and/or on chromosome 9, preferably at least one on both chromosome 6 and on chromosome 9 and at least one of the loci on chromosome 11.

Therefore, according to another embodiment of the invention, the QTLs present in the genome of a plant, seed or cell of the invention are preferably to be found at least at one or more of the 18 loci encompassing said 18 SNPs mentioned above, namely the locus encompassing TO-0005197 (SEQ ID NO:1), the locus encompassing TO-0145581 (SEQ ID NO:2) for QTL1 on chromosome 6, the locus encompassing TO-0180955 (SEQ ID NO:3), the locus encompassing TO-0196724 (SEQ ID NO:4), the locus encompassing TO-0145125 (SEQ ID NO:5), the locus encompassing TO-0196109 (SEQ ID NO:6), for QTL2 on chromosome 9, the locus encompassing TO-0122252 (SEQ ID NO:7), the locus encompassing TO-0144317 (SEQ ID NO:8), the locus encompassing TO-0142270 (SEQ ID NO:9), the locus encompassing TO-0142294 (SEQ ID NO:10), the locus encompassing TO-0142303 (SEQ ID NO:11), the locus encompassing TO-0142306 (SEQ ID NO:12), the locus encompassing TO-0182276 (SEQ ID NO:13), the locus encompassing TO-0181040 (SEQ ID NO:14), the locus encompassing TO-0123057 (SEQ ID NO:15), the locus encompassing TO-0125528 (SEQ ID NO:16), the locus encompassing TO-0162432 (SEQ ID NO:17) and the locus encompassing TO-0162427 (SEQ ID NO:18) for QTL3 on chromosome 11.

For a tomato plant according to the invention, the fruits of which have an improved tolerance when infected by the TBRFV, the QTLs present in the genome of a plant, seed or cell of the such tomato plant are preferably to be found at least at one or more of the following loci: the locus encompassing TO-0005197, the locus encompassing TO-0145581 for QTL1 on chromosome 6, and/or the locus encompassing TO-0180955, the locus encompassing TO-0196724, the locus encompassing TO-0145125 and the locus encompassing TO-0196109 for QTL2 on chromosome 9.

For a tomato plant according to the invention, the leaves of which have an improved tolerance when infected by the TBRFV, the QTLs present in the genome of a plant, seed or cell of the such tomato plant are preferably to be found at least at one or more of the following loci: the locus encompassing TO-0122252, the locus encompassing TO-0144317, the locus encompassing TO-0142270, the locus encompassing TO-0142294, the locus encompassing TO-0142303, the locus encompassing TO-0142306, the locus encompassing TO-0182276, the locus encompassing TO-0181040, the locus encompassing TO-0123057, the locus encompassing TO-0125528, the locus encompassing TO-0162432 and the locus encompassing TO-0162427 for QTL3 on chromosome 11.

For a tomato plant according to the invention having an improved tolerance in both its leaves and fruits when infected by the TBRFV, the QTLs present in the genome of a plant, seed or cell of the invention are preferably to be found at least at one or more of the 2 loci encompassing the SNPs on chromosome 6, namely the locus encompassing TO-0005197 and the locus encompassing TO-0145581, and/or at least at one or more of the 4 loci encompassing the SNPs on chromosome 9, namely the locus encompassing TO-0180955, the locus encompassing TO-0196724, the locus encompassing TO-0145125 and the locus encompassing TO-0196109, and also at least at one or more of the 12 loci encompassing the SNPs on chromosome 11, namely the locus encompassing TO-0122252, the locus encompassing TO-0144317, the locus encompassing TO-0142270, the locus encompassing TO-0142294, the locus encompassing TO-0142303, the locus encompassing TO-0142306, the locus encompassing TO-0182276,the locus encompassing TO-0181040, the locus encompassing TO-0123057, the locus encompassing TO-0125528, the locus encompassing TO-0162432 and the locus encompassing TO-0162427.

The alleles of the 18 SNPs of the invention corresponding to the QTLs conferring the TBRFV tolerance are allele T of TO-0005197, allele C of TO-0145581, allele G of TO-0180955, allele C of TO-0196724, allele G of TO-0145125, allele G of TO-0196109, allele T of TO-0122252, allele C of TO-0144317, allele T of TO-0142270, allele G of TO-0142294, allele A of TO-0142303, allele A of TO-0142306, allele G of TO-0182276, allele G of TO-0181040, allele G of TO-0123057, allele A of TO-0125528, allele C of TO-0162432 and allele T of TO-0162427. The presence of the QTLs conferring the tolerance to TBRFV can be revealed by the presence of said specific alleles. The alleles of these SNPs can thus reflect the presence of the QTLs of the invention.

According to a preferred embodiment of the present invention, the QTLs conferring the tolerance to TBRFV are on one or more chromosomal intervals delimited by the SNPs of the present invention.

According to this embodiment, the QTL1 is on a chromosomal interval of chromosome 6 delimited on one side by SNP TO-0005197 and on the other side by SNP TO-0145581.

According to another embodiment, the QTL2 is on a chromosomal interval of chromosome 9 delimited on one side by SNP TO-0180955 and on the other side by SNP TO-0196109.

According to another embodiment, the QTL3 is on a chromosomal interval of chromosome 11 delimited on one side by SNP TO-0122252 and on the other side by TO-0162427. More preferred chromosomal intervals of chromosome 11 within which QTL3 is to be found are the interval delimited by TO-0144317 and TO-0125528, the interval delimited by TO-0142270 and TO-0162432, the interval delimited by TO-0144317 and TO-0162432, and the interval delimited by TO-0142270 and TO-0125528. The even more preferred interval is the interval delimited by TO-0142270 and TO-0125528. Another preferred interval is the interval delimited by and comprising TO-0142294 and TO-0125528.

It is noted in this respect that specific positions in a chromosome can indeed be defined with respect to single nucleotide polymorphism, insofar as the flanking sequences of said SNPs are defined in order to unambiguously position them on the genome. The present inventors have used SNPs, identified by their flanking sequences, with different alleles, to identify and follow the QTLs of the present invention.

A chromosomal region delimited by two SNPs X and Y refers to the section of the chromosome lying between the positions of these two SNPs and comprising said SNPs, therefore the nucleotide sequence of this chromosomal region begins with the nucleotide corresponding to SNP X and ends with the nucleotide corresponding to SNP Y, i.e. the SNPs are comprised within the region they delimit, in the sense of the invention.

In a plant, seed or cell of the invention, the presence of the QTLs conferring the phenotype of interest is preferably characterized by TO-0005197 and/or TO-0145581 for the QTL1 on chromosome 6 and/or by TO-0180955, TO-0196724, TO-0145125 and/or TO-0196109 for the QTL2 on chromosome 9 when the tolerance to TBRFV is a fruit tolerance and preferably characterized by TO-0122252, TO-0144317, TO-0142270, TO-0142294, TO-0142303, TO-0142306, TO-0182276, TO-0181040, TO-0123057, TO-0125528, TO-0162432 and TO-0162427, most preferably by TO-0142294, TO-0142303, TO-0142306, TO-0182276, TO-0181040, TO-0123057, TO-0125528, and even more preferably TO-0182276, for the QTL3 on chromosome 11 when the tolerance to TBRFV is a foliar tolerance.

When present homozygously in the genome of a tomato plant according to the invention, QTL1 and/or QTL2 will confer independently and collectively fruit resistance/tolerance to TBRFV and QTL3 will confer leaf resistance/tolerance to TBRFV. When the three QTLs are present homozygously in the genome of a tomato plant according to the invention, or when QTL1 and QTL3, or QTL2 and QTL3 are present homozygously, such plant has an improved fruit and foliar tolerance to TBRFV.

The invention is also directed to hybrid plants of S. lycopersicum, obtainable by crossing a plant having the improved phenotype and bearing homozygously one or more of the QTLs of the invention, with another S. lycopersicum. The plant having the improved phenotype and bearing homozygously one or more of the QTLs of the invention could be a tomato plant having fruit tolerance to TBRFV and in such a case will bear homozygously QTL1 and/or QTL2, could be a tomato plant having leaf tolerance to TBRFV and in such a case will bear homozygously QTL3, or could be a plant having both fruit and foliar tolerance to TBRFV. In the latter case, the tomato plant will bear homozygously QTL1 and QTL3, QTL2 and QTL3, or QTL1, QTL2 and QTL3, preferably QTL1, QTL2 and QTL3. As the QTLs of the present invention act in a recessive manner, the hybrid plants of S. lycopersicum produced by the above described cross will have leaf and/or fruit tolerance to TBRFV only if the other S. lycopersicum crossing partner harbors the QTLs of the present invention. If the other *S. lycopersicum* crossing partner is devoid of the QTLs of the present invention, the hybrid resulting from the cross will harbor the QTLs of the present invention in a heterozygous manner and the tomato plants will not have the leaf and/or fruit tolerance. Resistant/tolerant progenies thereof would however be available to the breeder skilled in the art.

Preferably, a *S. lycopersicum* plant according to the invention is a commercial plant or line. Such a commercial plant or line preferably also exhibits resistance to ToMV (tomato mosaic virus), for example due to the presence of a Tm-2 (allele Tm-2 or Tm-22 (also known as Tm-2a)) or Tm-1 resistance gene, which also confers resistance to TMV (Tobacco Mosaic Virus). A plant according to this aspect of the invention preferably has also the following additional features: nematode resistance trait (Mi-1 or Mi-j), as well as Fusarium and Verticillium resistances.

Other resistances or tolerances are also envisaged according to the invention.

According to a preferred embodiment, a plant of the invention is not resistant to Pepino Mosaic Virus (PepMV). According to another embodiment, a tomato plant of the invention is also resistant to PepMV.

According to still another embodiment, a plant of the invention is a determinate, indeterminate or semi-indeterminate plant, or seed or cell thereof, i.e. corresponding to determinate, indeterminate or semi-indeterminate growth habit.

By determinate, it is meant tomato plants which tend to grow their foliage first, then set flowers that mature into fruit if pollination is successful. All of the fruits tend to ripen on a plant at about the same time. Indeterminate tomatoes start out by growing some foliage, then continue to produce foliage and flowers throughout the growing season. These plants will tend to have tomato fruit in different stages of maturity at any given time. The semi-determinate tomatoes have a phenotype between determinate and indeterminate, they are typical determinate types except that grow larger than determinate varieties.

According to still another embodiment, a plant of the invention is used as a scion or as a rootstock in a grafting process. Grafting is a process that has been used for many years in crops such as cucurbitacea, but only more recently for tomato. Grafting may be used to provide a certain level of resistance to telluric pathogens such as Phytophthora or to certain nematodes. Grating is therefore intended to prevent contact between the plant or variety to be cultivated and the infested soil. The variety of interest used as the graft or scion, optionally an F1 hybrid, is grafted onto the resistant plant used as the rootstock. The resistant rootstock remains healthy and provides, from the soils, the normal supply for the graft that it isolates from the diseases.

Moreover, the commercial plant of the invention gives rise to fruits in suitable conditions, which are at least 25 grams at full maturity, preferably at least 100 g at full maturity and or even more preferred at least 200 g at full maturity.

As detailed above, the invention is directed to *S. lycopersicum* plants, exhibiting the improved phenotype, as well as to seeds giving rise to those plants.

A plant or seed according to the invention may be a progeny or offspring of a plant grown from the deposited seeds HAZTBRFVRES1, deposited at the NCIMB under the accession number NCIMB 42758. Plants grown from the deposited seeds are indeed homozygous for the QTLs of the invention conferring the improved phenotype, they thus bear in their genome the QTLs of interest on each of the homologues of chromosome 6, 9 and 11. They can be used to transfer these sequences into another background by crossing and selfing and/ or backcrossing.

The invention is also directed to the deposited seeds of HAZTBRFVRES1 (NCIMB 42758) and to plants grown from one of these seeds. These seeds contain homozygously the QTLs conferring the phenotype of interest. It is noted that these seeds do not correspond to a plant variety, they are not homozygous for most of the genes except the QTLs of the invention; their phenotype is thus not fixed during propagation, except for the foliar and fruit resistance/tolerance of the invention; most of their phenotypic traits segregate during propagation, with the exception of TBRFV foliar and fruit resistance/tolerance of the invention.

The invention is also directed to plants or seeds as defined above, i.e. containing one, two or the three QTLs of interest in homozygous or heterozygous state, said sequences conferring the improved phenotype when present homozygously, which plants or seeds are obtainable by transferring the QTLs from a *S. lycopersicum* plant, representative seeds thereof were deposited under NCIMB accession NCIMB-42758, into another *S. lycopersicum* genetic background, for example by crossing said plant with a second tomato plant parent and selection of the plant bearing the QTLs responsible for the phenotype of interest. In such crossing, QTL1, QTL2 and/or QTL 3 or any combination thereof could be transferred. Preferably, to obtain a plant having fruit tolerance, QTL1 only, or QTL2 only, or both QTLs 1 and 2 will be transferred, to obtain a plant having leaf tolerance, QTL 3 will be transferred and to obtain a plant having both fruit and foliar tolerance, QTL1 and QTL3, QTL2 and QTL3 or QTL1, QTL2 and QTL3, preferably QTL1, QTL2 and QTL3 will be transferred from the deposited seeds of HAZTBRFVRES1 (NCIMB 42758).

It is noted that the seeds or plants of the invention may be obtained by different processes, and are not exclusively obtained by means of an essentially biological process.

According to such an aspect, the invention relates to a tomato plant or seed, preferably a non-naturally occurring tomato plant or seed, which may comprise one or more mutations in its genome, which provides the plant with a fruit and/or a foliar tolerance to Tomato Brown Rugose Fruit virus, which mutation is as present, for example, in the genome of plants of which a representative sample was deposited with the NCIMB under deposit number NCIMB 42758.

In another embodiment, the invention relates to a method for obtaining a tomato plant or seed carrying one or more mutations in its genome, which provides the plant with a fruit and/or a foliar tolerance to Tomato Brown Rugose Fruit virus. Such a method is illustrated in example 7 and may comprise:

a) treating M0 seeds of a tomato plant to be modified with a mutagenic agent to obtain M1 seeds;

b) growing plants from the thus obtained M1 seeds to obtain M1 plants;

c) producing M2 seeds by self-fertilisation of M1 plants; and d) optionally repeating step b) and c) n times to obtain M1+n seeds.

The M1+n seeds are grown into plants and submitted to Tomato Brown Rugose Fruit virus infection. The surviving plants, or those with the milder symptoms of TBRFV infection, are multiplied one or more further generations while continuing to be selected for their fruit and/or foliar tolerance to Tomato Brown Rugose Fruit virus.

In this method, the M1 seeds of step a) can be obtained via chemical mutagenesis such as EMS mutagenesis. Other chemical mutagenic agents include but are not limited to, diethyl sufate (des), ethyleneimine (ei), propane sultone, N-methyl-N-nitrosourethane (mnu), N-nitroso-N-methyl-urea (NMU), N-ethyl-N-nitrosourea(enu), and sodium azide.

Alternatively, the mutations are induced by means of irradiation, which is for example selected from x-rays, fast neutrons, UV radiation.

In another embodiment of the invention, the mutations are induced by means of genetic engineering. Such mutations also include the integration of sequences conferring the TBRFV fruit and/or foliar resistance, as well as the substitution of residing sequences by alternative sequences conferring the TBRFV fruit and/or foliar resistance or tolerance. Preferably, the mutations are the integration of one or more of QTL1, QTL2 and QTL3 as described above, in replacement of the homologous sequences of a S. lycopersicum plants. Even more preferably, the mutation is the substitution of the sequence comprised within SNP TO-0122252 (SEQ ID NO:7) and SNP TO-0162427(SEQ ID NO:18) on chromosome 11 of S. lycopersicum genome, or a fragment thereof, by the homologous sequence on chromosome 11 present in the genome of a plant of which a representative sample was deposited with the NCIMB under deposit number NCIMB 42758, wherein the sequence or fragment thereof confers foliar resistance to TBRFV.

The genetic engineering means which can be used include the use of all such techniques called New Breeding Techniques which are various new technologies developed and/or used to create new characteristics in plants through genetic variation, the aim being targeted mutagenesis, targeted introduction of new genes or gene silencing (RdDM). Example of such new breeding techniques are targeted sequence changes facilitated through the use of Zinc finger nuclease (ZFN) technology (ZFN-1, ZFN-2 and ZFN-3, see U.S. Pat. No. 9,145,565), Oligonucleotide directed mutagenesis (ODM), Cisgenesis and intragenesis, Grafting (on GM rootstock), Reverse breeding, Agro-infiltration (agro-infiltration "sensu stricto", agro-inoculation, floral dip), Transcription Activator-Like Effector Nucleases (TALENs, see U.S. Pat. Nos. 8,586,363 and 9,181,535), the CRISPR/Cas system (see U.S. Pat. Nos. 8,697,359; 8,771,945; 8,795,965; 8,865, 406; 8,871,445; 8,889,356; 8,895,308; 8,906,616; 8,932, 814; 8,945,839; 8,993,233; and 8,999,641), engineered meganuclease re-engineered homing endonucleases, DNA guided genome editing (Gao et al., Nature Biotechnology (2016)), and Synthetic genomics. A major part of targeted genome editing, another designation for New Breeding Techniques, is the applications to induce a DNA double strand break (DSB) at a selected location in the genome where the modification is intended. Directed repair of the DSB allows for targeted genome editing. Such applications can be utilized to generate mutations (e.g., targeted mutations or precise native gene editing) as well as precise insertion of genes (e.g., cisgenes, intragenes, or transgenes). The applications leading to mutations are often identified as site-directed nuclease (SDN) technology, such as SDN1, SDN2 and SDN3. For SDN1, the outcome is a targeted, non-specific genetic deletion mutation: the position of the DNA DSB is precisely selected, but the DNA repair by the host cell is random and results in small nucleotide deletions, additions or substitutions. For SDN2, a SDN is used to generate a targeted DSB and a DNA repair template (a short DNA sequence identical to the targeted DSB DNA sequence except for one or a few nucleotide changes) is used to repair the DSB: this results in a targeted and predetermined point mutation in the desired gene of interest. As to the SDN3, the SDN is used along with a DNA repair template that contains new DNA sequence (e.g. gene). The outcome of the technology would be the integration of that DNA sequence into the plant genome. The most likely application illustrating the use of SDN3 would be the insertion of cisgenic, intragenic, or transgenic expression cassettes at a selected genome location. A complete description of each of these techniques can be found in the report made by the Joint Research Center (JRC) Institute for Prospective Technological Studies of the European Commission in 2011 and titled "New plant breeding techniques—State-of-the-art and prospects for commercial development".

The invention in another aspect also concerns any plant likely to be obtained from seed or plants of the invention as described above, and also plant parts of such a plant, and most preferably explant, scion, cutting, seed, fruit, root, rootstock, pollen, ovule, embryo, protoplast, leaf, anther, stem, petiole, and any other plants part, wherein said plant, explant, scion, cutting, seed, fruit, root, rootstock, pollen, ovule, embryo, protoplast, leaf, anther, stem, petiole, and/or plant part is obtainable from a seed or plant according to the first aspect of the invention, i.e. bearing one, two or three of QTLs of interest, in whenever combination, homozygously or heterozygously in their genome. These plant parts, inter alia explant, scion, cutting, seed, fruit, root, rootstock, pollen, ovule, embryo, protoplast, leaf, anther, stem or petiole, comprise in their genome the QTLs conferring the phenotype of interest when present homozygously, i.e. fruit and/or foliar tolerance to TBRFV.

The QTLs referred to in this aspect of the invention are those defined above in the context of plants of the invention. The different features of the QTLs defined in relation with the first aspect of the invention apply mutatis mutandis to this aspect of the invention. The QTLs are thus preferably chosen from those present in the genome of a plant corresponding to the deposited material HAZTBRFVRES1 (NCIMB accession number 42758). They are advantageously characterized by the presence of allele T of TO-0005197, allele C of TO-0145581, allele G of TO-0180955, allele C of TO-0196724, allele G of TO-0145125, allele G of TO-0196109, allele T of TO-0122252, allele C of TO-0144317, allele T of TO-0142270, allele G of TO-0142294, allele A of TO-0142303, allele A of TO-0142306, allele G of TO-0182276, allele G of TO-0181040, allele G of TO-0123057, allele A of TO-0125528, allele C of TO-0162432 and/or allele T of TO-0162427, depending of the QTL of interest, and preferably by the presence of this or these alleles homozygously , namely the presence of the two alleles T of TO-0005197, of the two alleles C of TO-0145581, of the two alleles G of TO-0180955, of the two alleles C of TO-0196724, of the two alleles G of TO-0145125, of the two alleles G of TO-0196109, of the two alleles T of TO-0122252, of the two alleles C of TO-0144317, of the two alleles T of TO-0142270, of the two alleles G of TO-0142294, of the two alleles A of TO-0142303, of the two alleles A of TO-0142306, of the two alleles G of TO-0182276, of the two alleles G of TO-0181040, of the two alleles G of TO-0123057, of the two alleles A of TO-0125528, of the two alleles C of TO-0162432 and/or of the two alleles T of TO-0162427.

The invention is also directed to cells of S. lycopersicum plants, such that these cells comprise, in their genome, the QTLs of the present invention conferring the phenotype of interest to a S. lycopersicum plant, preferably these QTLs are present homozygously. The QTLs are those already defined in the frame of the present invention, they are characterized by the same features and preferred embodiments already disclosed with respect to the plants and seeds according to the preceding aspects of the invention. The presence of these QTLs can be revealed by the techniques disclosed above and well known to the skilled reader. It can inter alia be determined whether the QTLs are present homozygously or heterozygously in the genome of such a cell of the invention. They are advantageously characterized by the presence of allele T of TO-0005197, allele C of TO-0145581, allele G of TO-0180955, allele C of TO-0196724, allele G of TO-0145125, allele G of TO-0196109, allele T of TO-0122252, allele C of TO-0144317, allele T of TO-0142270, allele G of TO-0142294, allele A of TO-0142303, allele A of TO-0142306, allele G of TO-0182276, allele G of TO-0181040, allele G of TO-0123057, allele A of TO-0125528, allele C of TO-0162432 and/or allele T of TO-0162427, depending of the QTL of interest, and preferably by the presence of this or these alleles simultaneously on each chromosome, i.e. homozygously.

Cells according to the invention can be any type of *S. lycopersicum* cell, inter alia an isolated cell and/or a cell capable of regenerating a whole *S. lycopersicum* plant, bearing the QTLs of interest.

The present invention is also directed to a tissue culture of non-regenerable or regenerable cells of the plant as defined above according to the present invention; preferably, the regenerable cells are derived from embryos, protoplasts, meristematic cells, callus, pollen, leaves, anthers, stems, petioles, roots, root tips, fruits, seeds, flowers, cotyledons, and/or hypocotyls of the invention, and the cells contain one, two or three of the QTLs of interest, in whenever combination, homozygously or heterozygously in their genome conferring, when present homozygously the improved phenotype, namely fruit tolerance to TBRFV for QTL1 and/or QTL2, foliar tolerance to TBRFV for QTL3.

The tissue culture will preferably be capable of regenerating plants having the physiological and morphological characteristics of the foregoing tomato plant, and of regenerating plants having substantially the same genotype as the foregoing tomato plant. The present invention also provides tomato plants regenerated from the tissue cultures of the invention.

The invention also provides a protoplast of the plant defined above, or from the tissue culture defined above, said protoplast containing the QTLs conferring the improved phenotype of the invention.

According to another aspect, the present invention is also directed to the use of a tomato plant of the invention, preferably comprising homozygously the QTLs of the invention, as a breeding partner in a breeding program for obtaining *S. lycopersicum* plants having the improved phenotype of the invention. Indeed, such a breeding partner harbors homozygously in its genome the QTLs conferring the phenotype of interest. By crossing this plant with a tomato plant, especially a line, it is thus possible to transfer one, two or the three QTLs of the present invention conferring the desired phenotype, to the progeny. A plant according to the invention can thus be used as a breeding partner for introgressing QTLs conferring the desired phenotype into a *S. lycopersicum* plant or germplasm, preferably for transferring the QTL responsible for leaf resistance. Although a plant or seed bearing the QTLs of interest heterozygously, can also be used as a breeding partner as detailed above, the segregation of the phenotype is likely to render the breeding program more complex.

The improved phenotype of the invention is tolerance to TBRFV, inter alia foliar tolerance or fruit tolerance, or combination of fruit and foliar tolerance.

The introgressed QTLs will advantageously be introduced into varieties that contain other desirable genetic traits such as resistance to disease, early fruit maturation, drought tolerance, fruit shape, and the like.

The invention is also directed to the same use with plants or seed of HAZTBRFVRES1, deposited at the NCIMB under the accession number NCIMB 42758. Said plants are also suitable as introgression partners in a breeding program aiming at conferring the desired phenotype to a *S. lycopersicum* plant or germplasm.

In such a breeding program, the selection of the progeny displaying the desired phenotype, or bearing the QTLs linked to the desired phenotype, can advantageously be carried out on the basis of the alleles of the SNP markers, especially the SNP markers of the invention.

A progeny of the plant is preferably selected on the presence of allele T of TO-0005197 and/or allele C of TO-0145581 for the presence of QTL1 on chromosome 6, allele G of TO-0180955, allele C of TO-0196724, allele G of TO-0145125 and/or allele G of TO-0196109 for the presence of QTL2 on chromosome 9, allele T of TO-0122252, allele C of TO-0144317, allele T of TO-0142270, allele G of TO-0142294, allele A of TO-0142303, allele A of TO-0142306, allele G of TO-0182276, allele G of TO-0181040, allele G of TO-0123057, allele A of TO-0125528, allele C of TO-0162432 and/or allele T of TO-0162427 for the presence of QTL3 on chromosome 11. As per the recessive nature of the QTLs, the progeny of the plant is preferably selected on the presence of the same allele on both homologues of each chromosome.

The selection can alternatively be made on the basis of the presence of any one of the alleles of the 18 SNPs of the invention linked to the improved phenotype or a combination of these alleles. According to such an embodiment, the selection can be made on the presence of at least 1 SNP allele for QTL1, at least one SNP allele for QTL2 or at least one SNP allele for QTL3 or on the simultaneous presence of at least 1 SNP allele for QTL1, at least one SNP allele for QTL2 and/or at least one SNP allele for QTL3, depending on the QTLs combination to be achieved (QTL1 and QTL2, QTL1 and QTL3, QTL2 and QTL3, QTL1, QTL2 and QTL3, preferably QTL1, QTL2 and QTL3). Such selection will be made on the presence of the alleles of interest in a genetic material sample of the plant to be selected. The presence of these alleles indeed confirms the presence of QTLs of the invention at the loci defined by said SNPs. Moreover, further to point mutation or recombination event, it is conceivable that at least 1 or 2 of these alleles is lost, the remaining of the chromosomal fragment bearing the QTLs of interest still conferring the phenotype of interest.

A plant according to the invention, or grown from a seed as deposited under accession number NCIMB 42758, is thus particularly valuable in a marker assisted selection for obtaining commercial tomato lines and varieties, having the improved phenotype of the invention.

The invention is also directed to the use of said plants in a program aiming at identifying, sequencing and/or cloning the genetic sequences conferring the desired phenotype.

Any specific embodiment described for the previous aspects of the invention is also applicable to this aspect of the invention, especially with regard to the features of the QTLs conferring the phenotype of interest.

The invention is also directed to a method for identifying, detecting and/or selecting *S. lycopersicum* plants having the QTLs of the present invention as found in the genome of the seeds of HAZTBRFVRES1 (NCIMB accession number 42758), said QTLs conferring an improved phenotype of tolerance and/ resistant to Tomato Brown Rugose Fruit virus with respect to a corresponding plant devoid of said sequences, the method comprising the detection of at least one of the following markers: allele T of TO-0005197, allele C of TO-0145581, allele G of TO-0180955, allele C of TO-0196724, allele G of TO-0145125, allele G of TO-0196109, allele T of TO-0122252, allele C of TO-0144317, allele T of TO-0142270, allele G of TO-0142294, allele A of TO-0142303, allele A of TO-0142306, allele G of TO-0182276, allele G of TO-0181040, allele G of TO-0123057, allele A of TO-0125528, allele C of TO-0162432 or allele T of TO-0162427 in a genetic material sample of the plant to be identified and or selected.

The invention is also directed to a method for detecting or selecting *S. lycopersicum* plants having QTLs conferring resistance to TBRFV only when present homozygously and having at least one of the following alleles: allele T of TO-0005197, allele C of TO-0145581, allele G of TO-0180955, allele C of TO-0196724, allele G of TO-0145125, allele G of TO-0196109, allele T of TO-0122252, allele C of TO-0144317, allele T of TO-0142270, allele G of TO-0142294, allele A of TO-0142303, allele A of TO-0142306, allele G of TO-0182276, allele G of TO-0181040, allele G of TO-0123057, allele A of TO-0125528, allele C of TO-0162432 or allele T of TO-0162427), wherein the detection or selection is made on condition of TBRFV infection comprising inoculation of TBRFV on the plants to be tested. According to a preferred embodiment, the method is for detecting or selecting *S. lycopersicum* plants having a QTL conferring foliar resistance or tolerance to TBRFV only when present homozygously and having allele G of TO-0182276, wherein the detection or selection is made on conditions of TBRFV infection comprising inoculation of TBRFV on the leaves of the plants to be tested.

The method is particularly adapted in a breeding program with HAZTBRFVRES1 (NCIMB accession number 42758), as initial parent, or progeny thereof, comprising the QTLs of the invention conferring resistance, wherein the detection and/or selection is made on conditions comprising infestation by TBRFV and wherein said introgressed sequences confer resistance or tolerance to TBRFV and have at least one of the following markers: allele T of TO-0005197, allele C of TO-0145581, allele G of TO-0180955, allele C of TO-0196724, allele G of TO-0145125, allele G of TO-0196109, allele T of TO-0122252, allele C of TO-0144317, allele T of TO-0142270, allele G of TO-0142294, allele A of TO-0142303, allele A of TO-0142306, allele G of TO-0182276, allele G of TO-0181040, allele G of TO-0123057, allele A of TO-0125528, allele C of TO-0162432 or allele T of TO-0162427, and more preferably those of chromosome 11, and even more preferably allele G of TO-0182276.

The invention is moreover directed to a method for detecting and/or selecting *S. lycopersicum* plants having at least one of the QTLs of the present invention conferring the improved phenotype, on the basis of the allele detection of at least one SNP chosen amongst the 18 SNPs.

Preferably, plants bearing the QTLs of the present invention are selected if at least one of the following markers, and preferably at least 2, 3, 4, 5 or more or all, of allele T of TO-0005197, allele C of TO-0145581, allele G of TO-0180955, allele C of TO-0196724, allele G of TO-0145125, allele G of TO-0196109, allele T of TO-0122252, allele C of TO-0144317, allele T of TO-0142270, allele G of TO-0142294, allele A of TO-0142303, allele A of TO-0142306, allele G of TO-0182276, allele G of TO-0181040, allele G of TO-0123057, allele A of TO-0125528, allele C of TO-0162432 and/or allele T of TO-0162427, is/are detected, in a genetic material sample of the plant to be selected. A plant will be selected for the presence of QTL1 if at least one or both of the following alleles are detected: allele T of TO-0005197, allele C of TO-0145581. A plant will be selected for the presence of QTL2 if at least one or two, or three or four of the following alleles are detected: allele G of TO-0180955, allele C of TO-0196724, allele G of TO-0145125, allele G of TO-0196109. A plant will be selected for the presence of QTL3 if at least one or two, or three or four or five or more of the following alleles are detected: allele T of TO-0122252, allele C of TO-0144317, allele T of TO-0142270, allele G of TO-0142294, allele A of TO-0142303, allele A of TO-0142306, allele G of TO-0182276, allele G of TO-0181040, allele G of TO-0123057, allele A of TO-0125528, allele C of TO-0162432 and allele T of TO-0162427.

Plants will also be detected when having combination of the alleles of the present invention. A plant will be selected for the presence of QTL1 and QTL2 if at least one or both of the following alleles are detected: allele T of TO-0005197, allele C of TO-0145581 as well as at least one or two, or three or four of the following alleles are detected: allele G of TO-0180955, allele C of TO-0196724, allele G of TO-0145125, allele G of TO-0196109. A plant will be selected for the presence of QTL1 and QTL3 if at least one or both of the following alleles are detected: allele T of TO-0005197, allele C of TO-0145581 as well as at least one or two, or three or four or five or more of the following alleles are detected: allele T of TO-0122252, allele C of TO-0144317, allele T of TO-0142270, allele C of TO-0142294, allele A of TO-0142303, allele A of TO-0142306, allele G of TO-0182276, allele G of TO-0181040, allele G of TO-0123057, allele A of TO-0125528, allele C of TO-0162432 and allele T of TO-0162427. A plant will be selected for the presence of QTL2 and QTL3 if at least one or two, or three or four of the following alleles are detected : allele G of TO-0180955, allele C of TO-0196724, allele G of TO-0145125, allele G of TO-0196109, as well as at least one or two, or three or four or five or more of the following alleles are detected: allele T of TO-0122252, allele C of TO-0144317, allele T of TO-0142270, allele G of TO-0142294, allele A of TO-0142303, allele A of TO-0142306, allele G of TO-0182276, allele G of TO-0181040, allele A of TO-0123057, allele A of TO-0125528, allele C of TO-0162432 and allele T of TO-0162427. A plant will be selected for the presence of QTL1, QTL2 and QTL3 if at least one or both of the following alleles are detected : allele T of TO-0005197, allele C of TO-0145581 as well as one or two, or three or four of the following alleles are detected : allele G of TO-0180955, allele C of TO-0196724, allele G of TO-0145125, allele G of TO-0196109, as well as at least one or two, or three or four or five or more of the following alleles are detected: allele T of TO-0122252, allele C of TO-0144317, allele T of TO-0142270, allele G of TO-0142294, allele A of TO-0142303, allele A of TO-0142306, allele G of TO-0182276, allele G of TO-0181040, allele G of TO-0123057, allele A of TO-0125528, allele C of TO-0162432 and allele T of TO-0162427.

In all the previously described aspects of the invention, a preferred tolerance to TBRFV is foliar tolerance. Preferred SNPs are TO-0142294, TO-0142303, TO-0142306, TO-0182276, TO-0181040, TO-0123057 and TO-0125528, and even more preferablyTO-0182276, with respect to all the aspects of the invention.

The invention is further directed to a method for detecting and or selecting *S. lycopersicum* plants having at least one of the QTLs of the present invention conferring the improved phenotype, on the basis of the detection of any molecular marker revealing the presence of said QTLs. Indeed, now that the QTLs of the present invention have been identified by the present inventors, the identification and then the use of molecular markers, in addition to the 18 SNPs of the invention could be done by the skilled artisan. The QTLs themselves will continue to be characterized by the presence of at least one of the 18 SNPs of the invention, but they will also be identified through the use of different, alternative markers. Methods and uses of any such molecular markers for identifying the QTLs of the invention in a tomato genome, wherein said QTL confers foliar and/or fruit tolerance to TBRFV with respect to a corresponding plant devoid of said QTLs wherein said QTLs are characterized by the presence of at least one of the following SNPs: TO-0005197, TO-0145581, TO-0180955, TO-0196724, TO-0145125, TO-0196109, TO-0122252, TO-0144317, TO-0142270, TO-0142294, TO-0142303, TO-0142306, TO-0182276, TO-0181040, TO-0123057, TO-0125528, TO-0162432 and TO-0162427, are included in the present invention.

Are also included methods and uses of any such molecular markers for identifying the QTLs of the invention in a tomato genome, wherein said QTL confers foliar and/or fruit tolerance to TBRFV with respect to a corresponding plant devoid of said QTLs wherein said QTLs are characterized by the presence of at least one of the following SNP alleles: allele T of TO-0005197, allele C of TO-0145581, allele G of TO-0180955, allele C of TO-0196724, allele G of TO-0145125, allele G of TO-0196109, allele T of TO-0122252, allele C of TO-0144317, allele T of TO-0142270, allele G of TO-0142294, allele A of TO-0142303, allele A of TO-0142306, allele G of TO-0182276, allele G of TO-0181040, allele G of TO-0123057, allele A of TO-0125528, allele C of TO-0162432 and allele T of TO-0162427.

According to a still another aspect, the invention also concerns methods or processes for the production of *S. lycopersicum* plants having the desired phenotype, especially commercial plants and inbred parental lines. The present invention is indeed also directed to transferring one, two or three QTLs of the invention conferring the improved phenotype as defined, to other tomato varieties, or other species or inbred parental lines, and is useful for producing new types and varieties of tomatoes.

A method or process for the production of a plant having these features may comprise the following steps:

a) Crossing a plant grown from a deposited seed NCIMB 42758, or progeny thereof, bearing QTL1, QTL2 and/or QTL3 conferring TBRFV tolerance, and an initial *S. lycopersicum* plant, preferably devoid of said QTL(s), b) Selecting one plant in the progeny thus obtained, bearing one, two or three of the QTL1, QTL2 and/or QTL3 of the present invention;

c) Optionally self-pollinating one or several times the plant obtained at step b) and selecting in the progeny thus obtained a plant having tolerance to TBRFV, whether a fruit tolerance, a foliar tolerance or both, depending on the QTL(s) present in the progeny plant.

Alternatively, the method or process may comprise instead of step a) the following steps:

a1) Crossing a plant corresponding to the deposited seeds (NCIMB 42758), or progeny thereof, bearing QTL1, QTL2 and/or QTL3 conferring TBRFV tolerance, and an initial *S. lycopersicum* plant, preferably devoid of said QTL(s), a2) Increasing the F1 hybrid by means of selfing to create F2 population.

In the above methods or processes, SNPs markers are preferably used in steps b) and/or c), for selecting plants bearing sequences conferring the tolerance and or resistance phenotype of interest. The SNP markers are preferably one or more of the 18 SNP markers of the invention, including all combinations thereof as mentioned elsewhere in the present application.

According to a preferred embodiment, the selection for plant a having a foliar tolerance to the Tomato Brown Rugose Fruit virus is made on the basis of TO-0182276, or on the basis of at least one of TO-0142294, TO-0142303, TO-0142306, TO-0182276, TO-0181040, TO-0123057, TO-0125528. By selecting a plant on the basis of the allele of one or more SNPs, it is to be understood that the plant is selected as having tolerance to the TBRFV, whether a fruit tolerance/resistance, a foliar tolerance/resistance or both with respect to the initial plant, when the allele of the SNP(s) is (are) the allele corresponding to the allele of the HAZT-BRFVRES1 parent for this SNP and not the allele of the initial *S. lycopersicum* plant. For example, a plant can be selected as having the improved phenotype of the invention, when allele T of TO-0005197, allele C of TO-0145581, allele G of TO-0180955, allele C of TO-0196724, allele G of TO-0145125, allele G of TO-0196109, allele T of TO-0122252, allele C of TO-0144317, allele T of TO-0142270, allele G of TO-0142294, allele A of TO-0142303, allele A of TO-0142306, allele G of TO-0182276, allele G of TO-0181040, allele G of TO-0123057, allele A of TO-0125528, allele C of TO-0162432 and/or allele T of TO-0162427 is detected. Preferably, the *S. lycopersicum* plant of step a) is an elite line, used in order to obtain a plant with commercially desired traits or desired horticultural traits.

A method or process as defined above may advantageously comprises backcrossing steps, preferably after step c), in order to obtain plants having all the characterizing features of *S. lycopersicum* plants. Consequently, a method or process for the production of a plant having these features may also comprise the following additional steps:

d) Backcrossing the resistant plant selected in step b) or c) with a *S. lycopersicum* plant;

e) Selecting a plant bearing one, two or three of the QTL1, QTL2 and/or QTL3 of the present invention with respect to the initial plant.

The plant used in step a), namely the plant corresponding to the deposited seeds can be a plant grown from the deposited seeds; it may alternatively be any plant according to the 1st aspect of the invention, bearing the QTLs conferring the phenotype, preferably bearing these sequences homozygously.

At step e), SNPs markers can be used for selecting plants having a foliar tolerance and/or resistance to the Tomato Brown Rugose Fruit virus, with respect to the initial plant. The SNP markers are those of the invention, as described in the previous sections.

According to a preferred embodiment, the method or process of the invention is carried out such that, for at least one of the selection steps, namely b), c) and/or e), the selection is based on the detection of at least one of the following alleles: allele T of TO-0005197, allele C of TO-0145581, allele G of TO-0180955, allele C of TO-0196724, allele G of TO-0145125, allele G of TO-0196109, allele T of TO-0122252, allele C of TO-0144317, allele T of TO-0142270, allele G of TO-0142294, allele A of TO-0142303, allele A of TO-0142306, allele G of TO-0182276, allele G of TO-0181040, allele G of TO-0123057, allele A of TO-0125528, allele C of TO-0162432 and/or allele T of TO-0162427.

It is to be noted that, when plants having the improved phenotype, and bearing homozygously one or more of the QTL conferring this phenotype, are to be selected, the selection is to be made on the basis of one or more the SNPs of the invention, on the presence of the alleles representative of the QTLs, namely the alleles HAZTBRFVRES1 parent, coupled to the absence of the alleles representative of the recurrent *S. lycopersicum* parent.

The plant selected at step e) is preferably a commercial plant, especially a plant having fruits which weigh at least 25 g, at least 100 g or at least 200 g at full maturity in normal culture conditions.

Preferably, steps d) and e) are repeated at least twice and preferably three times, not necessarily with the same *S. lycopersicum* plant. Said *S. lycopersicum* plant is preferably a breeding line.

Resistance to nematode trait or resistance to ToMV may additionally be selected, at each selection step of the processes disclosed above.

The self-pollination and backcrossing steps may be carried out in any order and can be intercalated, for example a backcross can be carried out before and after one or several self-pollinations, and self-pollinations can be envisaged before and after one or several backcrosses.

The selection of the progeny having the desired improved phenotype can also be made on the basis of the comparison of the Tomato Brown Rugose Fruit virus resistance from the *S. lycopersicum* parent, through protocols as disclosed inter alia in the examples; the tested resistance/tolerance can be either fruit resistance/tolerance or foliar resistance/tolerance, or both.

The method used for allele detection can be based on any technique allowing the distinction between two different alleles of a SNP, on a specific chromosome.

The present invention also concerns a plant obtained or obtainable by such a method. Such a plant is indeed a *S. lycopersicum* plant having the improved phenotype according to the first aspect of the invention.

The invention is also directed to a method for obtaining commercial tomato plants or inbred parental lines thereof, having the desired improved phenotype, corresponding to a fruit and/or foliar tolerance and/or resistance to the Tomato Brown Rugose Fruit virus, with respect to an initial commercial *S. lycopersicum* plant, comprising the steps of:

a) Backcrossing a plant obtained by germinating a deposited seed HAZTBRFVRES1 NCIMB accession number 42758, or progeny thereof, bearing QTL1, QTL2 and/or QTL3 conferring TBRFV tolerance, with a commercial *S. lycopersicum* plant, b) Selecting a plant bearing one, two or three of the QTL1, QTL2 and/or QTL3 of the present invention.

Preferably, the selection is made on the basis of one or more of the 18 SNPs of the invention, as detailed for the other methods of the invention.

In all the methods and processes of the invention according to the invention, the initial *S. lycopersicum* plant is determinate, indeterminate or semi-determinate.

As already disclosed, the tomato plants according to the invention are preferably also resistant to Tomato Mosaic Virus, to nematodes, and to Fusarium and Verticillium. In order to obtain such plants in the processes and methods of the invention, the *S. lycopersicum* parents used in the breeding schemes are preferably bearing sequences conferring resistance to Tomato Mosaic Virus, to nematodes, and to Fusarium and Verticillium; and the selection steps are carried out to select plants having these resistance sequences, in addition to the QTL(s) conferring the improved phenotype of the invention.

The present invention is also directed to a *S. lycopersicum* plant and seed obtainable by any of the methods and processes disclosed above. The seed of such *S. lycopersicum* are preferably coated or pelleted with individual or combined active species such as plant nutrients, enhancing microorganisms, or products for disinfecting the environment of the seeds and plants. Such species and chemicals may be a product that promotes the growth of plants, for example hormones, or that increases their resistance to environmental stresses, for example defense stimulators, or that stabilizes the pH of the substrate and its immediate surroundings, or alternatively a nutrient.

They may also be a product for protecting against agents that are unfavorable toward the growth of young plants, including herein viruses and pathogenic microorganisms, for example a fungicidal, bactericidal, hematicidal, insecticidal or herbicidal product, which acts by contact, ingestion or gaseous diffusion; it is, for example, any suitable essential oil, for example extract of thyme. All these products reinforce the resistance reactions of the plant, and/or disinfect or regulate the environment of said plant. They may also be a live biological material, for example a nonpathogenic microorganism, for example at least one fungus, or a bacterium, or a virus, if necessary with a medium ensuring its viability; and this microorganism, for example of the pseudomonas, bacillus, trichoderma, clonostachys, fusarium, rhizoctonia, etc. type stimulates the growth of the plant, or protects it against pathogens.

In all the previous methods and processes, the identification of the plants bearing homozygously the QTLs responsible for the fruit and/or foliar tolerance to the TBRFV could be done by the detection of at least one of the alleles linked with each of the QTLs, but also in combination with the absence of the other allelic form of the SNPs of the present invention. As such, the identification of a plant bearing homozygously QTL1 of the present invention will be based on the identification of allele T of TO-0005197 and/or allele C of TO-0145581 as well as the absence of allele C of TO-0005197 and allele T of TO-0145581. Similarly, the identification of a plant bearing homozygously QTL2 of the present invention will be based on the identification of allele G of TO-0180955 and/or allele C of TO-0196724 and/or allele G of TO-0145125 and/or allele G of TO-0196109 as well as the absence of A of TO-0180955, allele T of TO-0196724, allele A of TO-0145125 and allele T of TO-0196109. Similarly, the identification of a plant bearing homozygously QTL3 of the present invention will be based on the identification of allele T of TO-0122252, and/or allele C of TO-0144317, and/or allele T of TO-0142270, and/or allele G of TO-0142294, and/or allele A of TO-0142303, and/or allele A of TO-0142306, and/or allele G of TO-0182276, and/or allele G of TO-0181040, and/or allele G of TO-0123057, and/or allele A of TO-0125528, and/or allele C of TO-0162432 and/or allele T of TO-0162427 as well as the absence of allele A of TO-0122252, allele T of TO-0144317, allele C of TO-0142270, allele A of TO-0142294, allele C of TO-0142303, allele G of TO-0142306, allele A of TO-0182276, allele A of TO-0181040, allele T of TO-0123057, allele G of TO-0125528, allele T of TO-0162432 and allele C of TO-0162427.

The invention is also directed to the use of the information provided herewith by the present inventors, namely the existence of 3 QTLs, present in the deposited seeds of HAZTBRFVRES1, and conferring the improved phenotype to *S. lycopersicum* plants, and the disclosure of molecular markers associated to these QTLs. This knowledge can be used inter alia for precisely mapping the QTLs, for defining their sequences, for identifying tomato plants comprising the QTLs conferring the improved phenotype and for identifying further or alternative markers associated to these QTLs. Such further markers are characterized by their location, namely close to the 18 markers disclosed in the present invention, and preferably from the 12 SNPs on chromosome 11, and by their association with the phenotype of interest, revealed by the invention, namely tolerance to TBRFV, either foliar tolerance, or fruit tolerance, or both.

By association, or genetic association, and more specifically genetic linkage, it is to be understood that a genetic polymorphism of the marker (i.e. a specific allele of the SNP marker) and the phenotype of interest occur simultaneously, i.e. are inherited together, more often than would be expected by chance occurrence, i.e. there is a non-random association of the allele and of the genetic sequences responsible for the phenotype, as a result of their proximity on the same chromosome.

A molecular marker of the invention, either one of 18 markers disclosed above or alternative markers, are inherited with the phenotype of interest in preferably more than 90% of the meioses, preferably in more than 95%, 96%, 98% or 99% of the meioses.

The invention thus concerns the use of one or more molecular markers, for fine-mapping or identifying a QTL in the tomato genome, said QTL conferring the improved phenotype of the invention to *S. lycopersicum* plants when present homozygoulsy, wherein said one or more markers is/are localized in one of the following chromosomal regions:

- in the chromosomal region delimited on chromosome 6 by TO-0005197 and TO-015581,
- in the chromosomal region delimited on chromosome 9 by TO-0180955 and TO-0196109,
- in the chromosomal region delimited on chromosome 11 by TO-0122252 and TO-0162427, or by TO-0142270 and TO-0125528, or
- at less than 2 megabase units from the locus of one of the 18 SNP markers of the invention, namely TO-0005197, TO-015581, TO-0180955, TO-0196724, TO-0145125, TO-0196109, TO-0122252, TO-0144317, TO-0142270, TO-0142294, TO-0142303, TO-0142306, TO-0182276, TO-0181040, TO-0123057, TO-0125528, TO-0162432 and TO-0162427.

The improved phenotype is tolerance to TBRFV, either fruit or foliar tolerance.

For fine-mapping or identifying a QTL conferring more specifically fruit tolerance, said one or more markers are localized in the chromosomal regions of chromosome 6 and 9 defined above or at less than 2 megabases from the locus of TO-0005197, TO-015581, TO-0180955, TO-0196724, TO-0145125 or TO-0196109. For fine-mapping or identifying a QTL conferring more specifically foliar tolerance, said one or more markers are localized in the chromosomal region of chromosome 11 defined above or at less than 2 megabases from the locus of TO-0122252, TO-0144317, TO-0142270, TO-0142294, TO-0142303, TO-0142306, TO-0182276, TO-0181040, TO-0123057, TO-0125528, TO-0162432 and TO-0162427.

According to a preferred embodiment, said one or more markers are in the chromosomal region delimited by TO-0122252 and TO-0162427, or by TO-0144317 and TO-0125528, or by TO-0142270 and TO-0162432, or by TO-0144317 and TO-0162432, or by TO-0142270 and TO-0125528.

Said one or more molecular marker(s) is/are moreover preferably associated, with a p-value of 0.05 or less, with at least one of the following SNP alleles: allele T of TO-0005197, allele C of TO-0145581, allele G of TO-0180955, allele C of TO-0196724, allele G of TO-0145125, allele G of TO-0196109, allele T of TO-0122252, allele C of TO-0144317, allele T of TO-0142270, allele G of TO-0142294, allele A of TO-0142303, allele A of TO-0142306, allele G of TO-0182276, allele G of TO-0181040, allele G of TO-0123057, allele A of TO-0125528, allele C of TO-0162432 and/or allele T of TO-0162427.

The molecular marker is preferably a SNP marker. It is more preferably at less than 1 megabase from the locus of at least one of the 18 SNPs of the invention.

The QTL are to be found in the deposited seeds NCIMB 42758.

The p-value is preferably less than 0.01.

The invention is also directed to the use of at least one of the SNP markers of the list TO-0005197, TO-015581, TO-0180955, TO-0196724, TO-0145125, TO-0196109, TO-0122252, TO-0144317, TO-0142270, TO-0142294, TO-0142303, TO-0142306, TO-0182276, TO-0181040, TO-0123057, TO-0125528, TO-0162432 and TO-0162427, associated with QTLs on chromosome 6 (the first two SNPs of the list), chromosome 9 ($3r^d$ to 6th SNP of the list) and chromosome 11 (7th to last SNP of the list) conferring the improved phenotype according to the invention, for identifying alternative molecular markers associated with said QTLs, wherein said alternative molecular markers are:

in the chromosomal region delimited on chromosome 6 by TO-0005197 and TO-015581, in the chromosomal region delimited on chromosome 9 by TO-0180955 and TO-0196109, in the chromosomal region delimited on chromosome 11 by TO-0122252 and TO-0162427, or by TO-0142270 and TO-0125528, or at less than 2 megabase units from the locus of 18 SNP markers of the invention, namely TO-0005197, TO-015581, TO-0180955, TO-0196724, TO-0145125, TO-0196109, TO-0122252, TO-0144317, TO-0142270, TO-0142294, TO-0142303, TO-0142306, TO-0182276, TO-0181040, TO-0123057, TO-0125528, TO-0162432 and TO-0162427.

According to a preferred embodiment, said alternative markers are in the chromosomal region delimited by TO-0122252 and TO-0162427, or by TO-0144317 and TO-0125528, or by TO-0142270 and TO-0162432, or by TO-0144317 and TO-0162432, or by TO-0142270 and TO-0125528.

The alternative molecular markers are preferably associated with said QTL(s) with a p-value of 0.05 or less, preferably less than 0.01. The QTLs are to be found in the deposited seeds NCIMB 42758. The invention is also directed to a method for identifying a molecular marker associated with a QTL conferring fruit tolerance to TBRFV when present homozygously, comprising:

identifying a molecular marker in the chromosomal region delimited on chromosome 6 by the SNP markers TO-0005197 and TO-015581, or in the chromosomal region delimited on chromosome 9 by the SNPs TO-0180955 and TO-0196109 or at less than 2 megabase unit from the locus of at least one of the SNP markers TO-0005197, TO-015581, TO-0180955, TO-0196724, TO-0145125 and TO-0196109; and determining whether said molecular marker is associated with or linked to the fruit tolerance to TBRFV in a segregating population issued from a plant exhibiting said improved phenotype. The population is preferably issued from a plant grown from the deposited seeds NCIMB 42758 or from a progeny thereof, exhibiting the fruit tolerance of the invention.

The QTLs on chromosome 6 and 9 mentioned above, conferring the fruit tolerance according to the invention, are the QTLs present in HAZTBRFVRES1 (NCIMB 42758).

Genetic association or linkage is as defined above; preferably the association or linkage is with a p-value of preferably less than 0.05, and most preferably less than 0.01 or even less.

A molecular marker and the resistance phenotype are inherited together in preferably more than 90% of the meioses, preferably more than 95%.

The invention is also directed to a method for identifying a molecular marker associated with a QTL conferring foliar tolerance to TBRFV when present homozygously, comprising:

identifying a molecular marker in the chromosomal region delimited on chromosome 11 by the SNP markers TO-0122252 and TO-0162427, or by TO-0142270 and TO-0125528, or at less than 2 megabase unit from the locus of at least one of the SNP markers TO-0122252, TO-0144317, TO-0142270, TO-0142294, TO-0142303, TO-0142306, TO-0182276, TO-0181040, TO-0123057, TO-0125528, TO-0162432 and TO-0162427; and determining whether said molecular marker is associated with or linked to the foliar tolerance to TBRFV in a segregating population issued from a plant exhibiting said improved phenotype. The population is preferably issued from a plant grown from the deposited seeds NCIMB 42758 or from a progeny thereof, exhibiting the foliar tolerance of the invention.

The QTL on chromosome 11 mentioned above, conferring the foliar tolerance according to the invention, is the QTL present in HAZTBRFVRES1 (NCIMB 42758).

The molecular markers according to this aspect of the invention are most preferably SNP markers. They are more preferably at less than 1 megabase from the locus of at least one of the 18 SNPs of the invention.

The invention is also directed to the use of a molecular marker for identifying or selecting a tomato plant comprising, in its genome, a QTL conferring fruit tolerance to TBRFV to *S. lycopersicum* plants when present homozygously, wherein said marker is localized in the chromosomal region delimited on chromosome 6 by the SNP markers TO-0005197 and TO-015581, or in the chromosomal region delimited on chromosome 9 by the SNPs TO-0180955 and TO-0196109 or at less than 2 megabase unit from the locus of at least one of the SNP markers TO-0005197, TO-015581, TO-0180955, TO-0196724, TO-0145125 and TO-0196109; and wherein said molecular marker is associated with at least one of the following SNP alleles: allele T of TO-0005197, allele C of TO-0145581, allele G of TO-0180955, allele C of TO-0196724, allele G of TO-0145125 and allele G of TO-0196109, with a p-value of 0.05 or less, preferably 0.01 or less. The fruit tolerance to TBRFV phenotype is conferred when the QTL is present homozygously.

The invention is also directed to the use of a molecular marker for identifying or selecting a tomato plant comprising, in its genome, a QTL conferring foliar tolerance to TBRFV to *S. lycopersicum* plants when present homozygously, wherein said marker is localized in the chromosomal region delimited on chromosome 11 by the SNP markers TO-0122252 and TO-0162427, or at less than 2 megabase unit from the locus of at least one of the SNP markers TO-0122252, TO-0144317, TO-0142270, TO-0142294, TO-0142303, TO-0142306, TO-0182276, TO-0181040, TO-0123057, TO-0125528, TO-0162432 and TO-0162427; and wherein said molecular marker is associated with at least one of the following SNP alleles: allele T of TO-0122252, allele C of TO-0144317, allele T of TO-0142270, allele G of TO-0142294, allele A of TO-0142303, allele A of TO-0142306, allele G of TO-0182276, allele G of TO-0181040, allele G of TO-0123057, allele A of TO-0125528, allele C of TO-0162432 and/or allele T of TO-0162427, with a p-value of 0.05 or less, preferably 0.01 or less. The foliar tolerance to TBRFV phenotype is conferred when the QTL is present homozygously.

The molecular marker to be used according to this embodiment is obtainable inter alia by the method for identifying further or alternative molecular markers, as disclosed above. The molecular marker is preferably a SNP marker. They are more preferably at less than 1 megabase from the locus of at least one of the 18 SNPs of the invention.

According to still another aspect, the invention is also directed to a method for genotyping a plant, preferably a S. lycopersicum plant or tomato germplasm, for the presence of at least one genetic marker associated with resistance or tolerance to TBRFV infection, wherein the method comprises the determination or detection in the genome of the tested plant of a nucleic acid comprising at least one of the markers of the invention, or comprising at least one of the alternative molecular markers as disclosed above. Preferably, the method comprises the step of identifying in a sample of the plant to be tested specific sequences associated with resistance/tolerance to TBRFV, in nucleic acid comprising at least one of allele T of TO-0005197, allele C of TO-0145581, allele G of TO-0180955, allele C of TO-0196724, allele G of TO-0145125, allele G of TO-0196109, allele T of TO-0122252, allele C of TO-0144317, allele T of TO-0142270, allele G of TO-0142294, allele A of TO-0142303, allele A of TO-0142306, allele G of TO-0182276, allele G of TO-0181040, allele G of TO-0123057, allele A of TO-0125528, allele C of TO-0162432 and/or allele T of TO-0162427. More preferably, the method comprises the detection in a sample of the plant to be tested of specific sequences associated with resistance to TBRFV in nucleic acid comprising allele T of TO-0122252, allele C of TO-0144317, allele T of TO-0142270, allele G of TO-0142294, allele A of TO-0142303, allele A of TO-0142306, allele G of TO-0182276, allele G of TO-0181040, allele G of TO-0123057, allele A of TO-0125528, allele C of TO-0162432 and/or allele T of TO-0162427.

According to a most preferred embodiment of this method, the method comprises the detection in the tested plant of the presence of nucleic acid comprising allele G of TO-0182276.

The detection of a specific allele of a SNP can be carried out by any method well known to the skilled reader.

In view of the ability of the resistant plants of the invention to restrict the damages caused by TBRFV infection, they are advantageously grown in an environment infested or likely to be infested or infected by TBRFV; in these conditions, the resistant or tolerant plants of the invention produce more marketable tomatoes than susceptible plants. The invention is thus also directed to a method for improving the yield of tomato plants in an environment infested by TBRFV comprising growing tomato plants comprising homozygously in their genome a QTL on chromosome 6, on chromosome 9 and/or on chromosome 11, as defined according to the previous aspects of the invention, and conferring to said plants resistance or tolerance to TBRFV. Preferably, the method comprises a first step of choosing or selecting a tomato plant having homozygously one or more of the QTLs of interest. The method can also be defined as a method of increasing the productivity of a tomato field, tunnel or glasshouse.

According to an embodiment, the method comprises growing a tomato plant comprising QTL3 as defined above on chromosome 11, conferring foliar resistance to TBRFV.

The invention is also directed to a method for reducing the loss on tomato production in condition of TBRFV infestation or infection, comprising growing a tomato plant as defined above.

These methods are particularly valuable for a population of tomato plants, either in a field, in tunnels or in glasshouses.

Alternatively, said methods for improving the yield or reducing the loss on tomato production may comprise a first step of identifying tomato plants resistant/tolerant to TBRFV and comprising in their genome a QTL on chromosome 6, 9 and/or 11 that confers to said plants a resistance or tolerance to said TBRFV, and then growing said resistant or tolerant plants in an environment infested or likely to be infested by the virus. Preferably, the plants comprise a QTL on chromosome 11 as defined according to the invention and conferring foliar tolerance to TBRFV when present homozygously. According to a preferred embodiment, the plants to be identified at the first step comprise allele G of TO-0182276.

The resistant plants of the invention are also able to restrict the growth of TBRFV, thus limiting the infection of further plants and the propagation of the virus. Accordingly, the invention is also directed to a method of protecting a field, tunnel or glasshouse, or any other type of plantation, from TBRFV infestation, or of at least limiting the level of infestation by TBRFV of said field, tunnel or glasshouse or of limiting the spread of TBRFV in a field, tunnel or glasshouse, especially in a tomato field. Such a method preferably comprises the step of growing a resistant or tolerant plant of the invention, i.e.

a plant comprising homozygously in its genome a QTL on chromosome 6, 9 and/or 11, conferring to said plant a resistance or tolerance to TBRFV. The plant of the invention to be used preferably comprises QTL3 on chromosome 11; more preferably the plant exhibits allele G of TO-0182276.

Preferably, the method comprises a first step of choosing or selecting a tomato plant having homozygously the QTLs of interest, especially QTL3 on chromosome 11.

The invention also concerns the use of a plant resistant or tolerant to TBRFV for controlling TBRFV infection or infestation in a field, tunnel or glasshouse, or other plantation; such a plant is a plant of the invention, comprising homozygously in its genome at least one of QTL1, QTL2, and/or QTL3 as defined above, on chromosomes 6, 9 and 11 respectively. According to this use, the plants of the invention are therefore used for protecting a field, tunnel or glasshouse from TBRFV infestation. The plants of the invention to be used preferably comprises QTL3 on chromosome 11; more preferably they exhibit allele G of TO-0182276.

Legend of Figures

FIG.1: p-value plot of QTL associated to fruit TBRFV resistance based on F2 population of HAZ1×HAZ2.

This figure is the Manhattan plot showing mapping results of the bi parental mapping population regarding (HAZ1× HAZ2, see example 4) the fruit tolerance and/or resistance to Tomato Brown Rugose Fruit virus. Vertical axis (y-axis) shows the −log 10 (p-value) and horizontal axis (x-axis) represents all SNPs by their positions (in physical distances bp) by chromosomes along the physical map.

Figure 2:
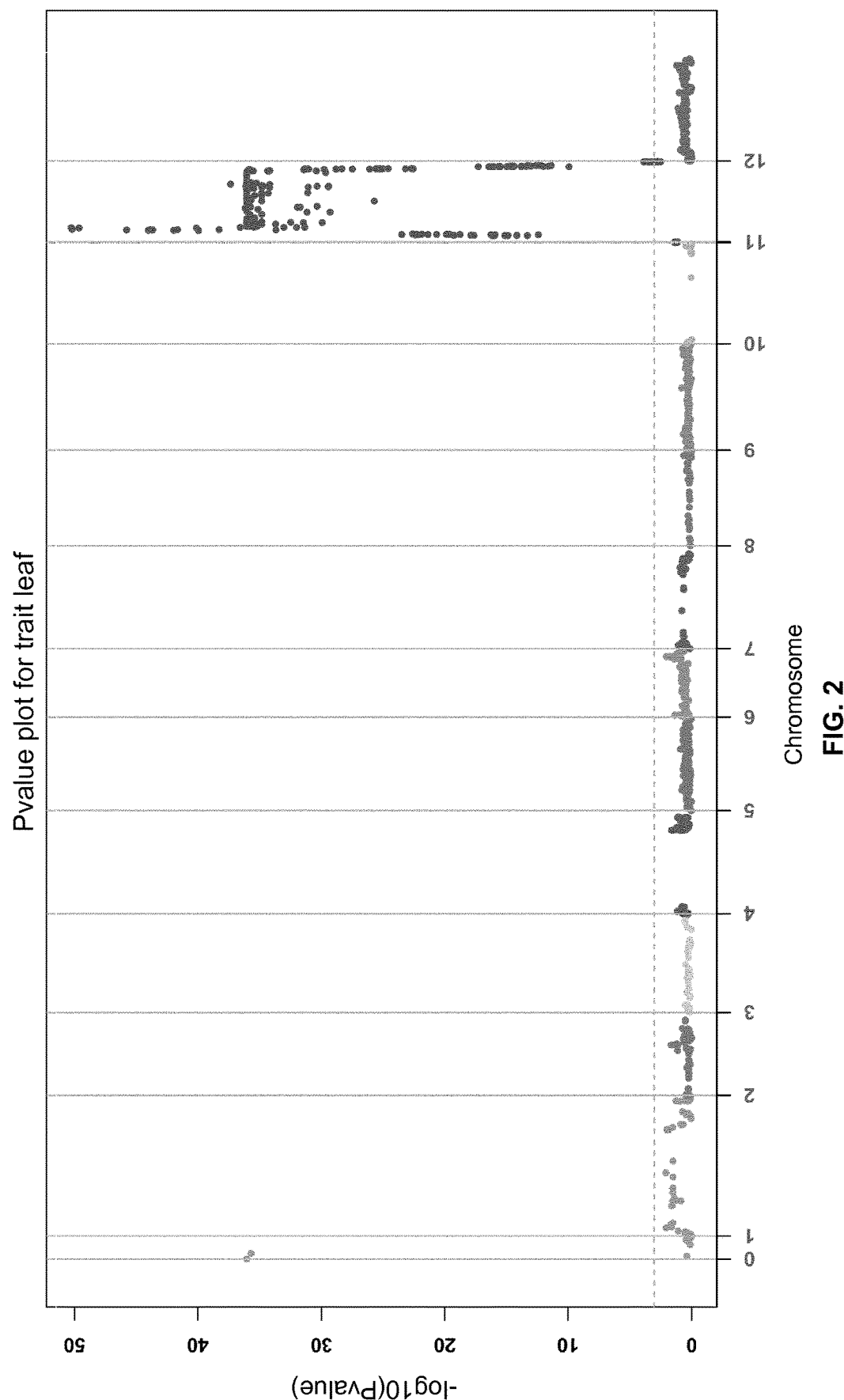

FIG.2: p-value plot of QTL associated to foliar TBRFV resistance based on F2 population of HAZ1×HAZ2.

This figure is the Manhattan plot showing mapping results of the bi parental mapping population (HAZ1×HAZ2, see example 4) regarding the leaf tolerance and/or resistance to Tomato Brown Rugose Fruit virus. Vertical axis (y-axis) shows the −log 10 (p-value) and horizontal axis (x-axis) represents all SNPs by their positions (in physical distances bp) by chromosomes along the physical map.

Figure 3:
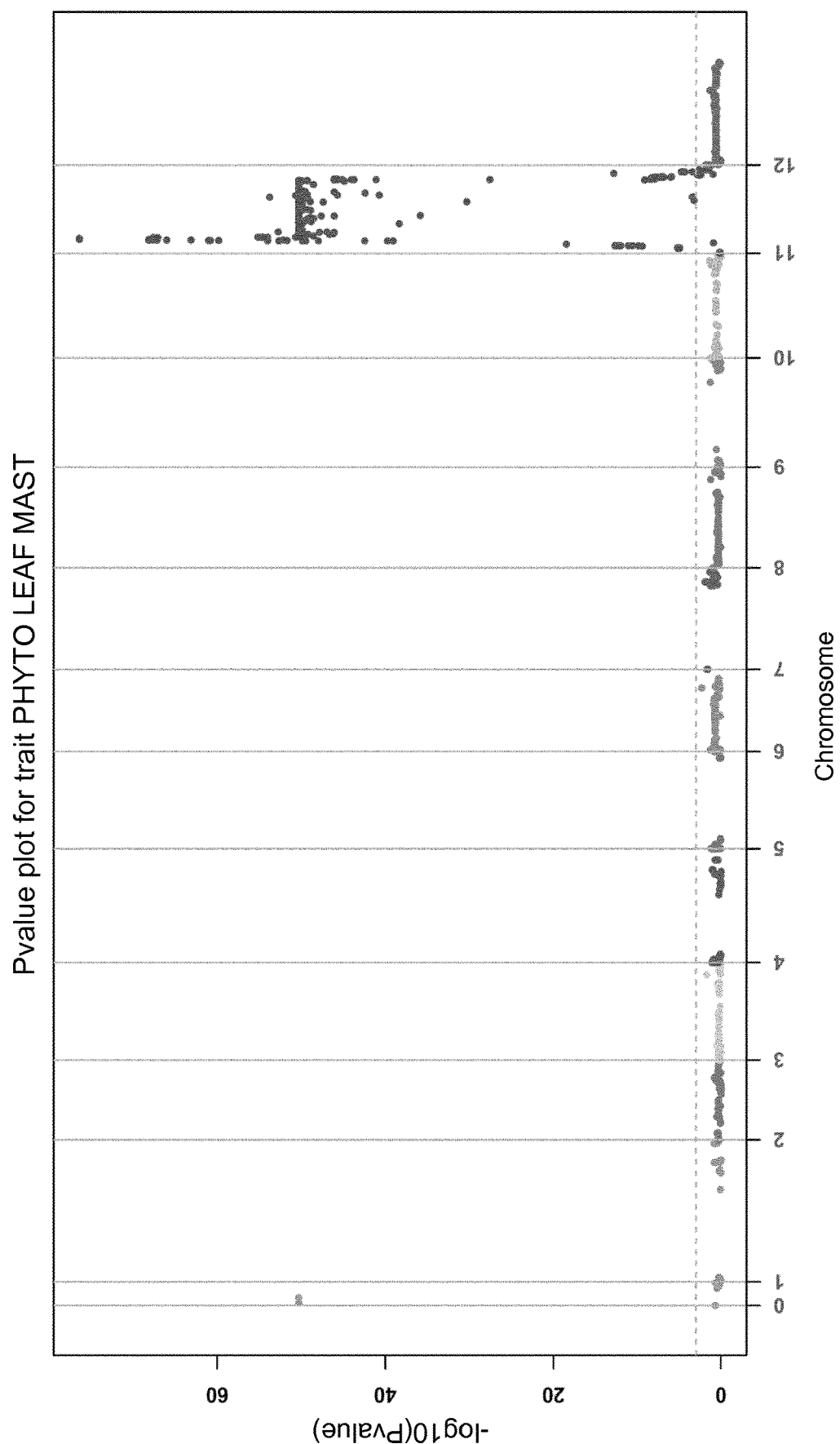

FIG.3: p-value plot of QTL associated to foliar TBRFV resistance based on F2 population of HAZ3×HAZ4

This figure is the Manhattan plot showing mapping results of the bi parental mapping population (HAZ3×HAZ4, see example 6) regarding the leaf tolerance and/or resistance to Tomato Brown Rugose Fruit virus. Vertical axis (y-axis) shows the −log 10 (p-value) and horizontal axis (x-axis) represents all SNPs by their positions (in physical distances bp) by chromosomes along the physical map.

EXAMPLES

Example 1: Collection and Identification of the Tomato Brown Rugose Fruit Virus

The present inventors have made a collection of different isolates from different Israeli production areas (North, Center and South Israel) infected by the Tomato Brown Rugose Fruit virus: 7 different isolates were collected and analyzed according to the protocols described in Salem et al. Sequences comparisons to the Jordanian Tomato Brown Rugose fruit virus showed that all Israeli isolates were identical to the Jordanian one, confirming the same virus was present in both countries.

Example 2: Identification of Resistance

The inventors have screened their tomato breeding genetic material in a naturally infected greenhouse in the Southern part of Israel, in the Bsor region, which is the major tomato crop production area in Israel. About 443 different tomatoes were screened. Each tomato was planted in two repeats, 10 plant per repeat in different locations in the greenhouse.

Each row in the greenhouse contained 120 plants. At each row, a susceptible line control of 10 plants was planted. In order to spread the controls in the different places in the greenhouse, the controls were positioned in diagonal along the different rows in the greenhouse.

In this screening, a few tomatoes showed no foliar TBRFV symptoms and very little fruit symptoms. Out of these, two symptomless tomatoes and two susceptible tomatoes were chosen for the next stage.

The results of these experiments are shown in table no. 1. The 2 susceptible tomatoes that have been chosen are representative of the 441 susceptible tomatoes in the sense that they are considered susceptible to the Tomato Brown Rugose fruit virus.

Hazera no. 1 (or HAZ1) is an indeterminate tomato of the loose type with regular, round and dark red fruits of about 170gr The plant has a dark green foliage and is resistant to Verticillium dahlia, Meloidogyne incognita, Tomato yellow leaf curl virus and Stemphylium solani.

Hazera no. 2 (or HAZ2) is an indeterminate tomato of the beef type with regular and intermediate flat, dark intense red fruits of about 280gr The plant is resistant to Verticillium dahlia, Fusarium oxysporum f.sp. *lycopersici* 1,2, Tomato mosaic virus, Fulvia fulva, Meloidogyne incognita, Tomato spotted wilt virus.

Hazera no. 3 (or HAZ3) is an indeterminate tomato of the beef type with intermediate flat red fruits of about 270gr The plant is resistant to Tomato spotted wilt virus, Verticillium dahlia Fusarium oxysporum f.sp. lycopersici 1,2 and Stemphylium solani.

Hazera no. 4 (or HAZ4) is an indeterminate tomato of the minibeef type with round red fruits of about 180gr The plant is resistant to Tobacco mosaic virus, Tomato yellow leaf curl virus, Cladosporium fulvum (CF9) Verticillium dahlia and Fusarium oxysporum f.sp. *lycopersici* 1,2.

TABLE 1

| | plants tested for resistance to TBRFV: | | |
|---|---|---|---|
| Tomato | Total number of plants | Nb of plants without TBRFV foliar and fruit symptoms | Nb of plants with significant TBRFV foliar and fruit symptoms | Conclusion |
| Hazera no. 1 | 20 | 20 | 0 | Tolerant/Resistant |
| Hazera no. 2 | 20 | 0 | 20 | Susceptible |
| Hazera no. 3 | 20 | 20 | 0 | Tolerant/Resistant |
| Hazera no. 4 | 20 | 0 | 20 | Susceptible |

Example 3: Confirmation of Resistance

In order to better understand the genetics underlying the tolerance/resistance phenotype as well as to validate the leads identified during the first screening, the present inventors have made a second screening under similar conditions as the ones of the first screening : each row in the greenhouses under natural infection contained 120 plants and at each row, a susceptible control (10 plants) was planted. In order to spread the controls in the different places in the greenhouse, the controls were positioned in diagonal along the different rows in the greenhouse.

In addition to the resistant tomatoes identified during the first screening, their F1 obtained from the cross of a resistant plant with a susceptible line were also included in the trial, as well as their F2s:

Table 2 shows the result of the second screening regarding the foliar evaluation : plants were considered as susceptible as soon as they had some mosaic and distortions in the apex of the shoots. Tolerant/Resistant plants have no symptoms in the apex of the shoots.

TABLE 2

Foliar evaluation of second screening

| Tomato | Total number of plants | Number of plants without TBRFV foliar symptoms | Number of plants with significant TBRFV foliar symptoms | Conclusion |
|---|---|---|---|---|
| Hazera no. 1 | 20 | 20 | 0 | Tolerant/Resistant |
| Hazera no. 2 | 20 | 0 | 20 | Susceptible |
| F1 Hazera no. 1 × Hazera no. 2 | 20 | 0 | 20 | Susceptible |
| F2 Hazera no. 1 × Hazera no. 2 | 247 | 60 | 187 | Segregating |
| Hazera no. 3 | 20 | 20 | 0 | Tolerant/Resistant |
| Hazera no. 4 | 20 | 0 | 20 | Susceptible |
| F1 Hazera no. 3 × Hazera no. 4 | 20 | 0 | 20 | Susceptible |
| F2 Hazera no. 3 × Hazera no. 4 | 248 | 63 | 185 | Segregating |

The phenotyping data of the F1 and F2 plants tend to demonstrate that the foliar tolerance and or resistance to the Tomato Brown Rugose fruit virus is controlled in a recessive manner by one single gene or QTL.

Table 3 shows the result of the second screening regarding the fruit evaluation : plants are scored on a 1 to 4 scale whereby plants with 1 to 3 scores will be considered as susceptible, having for the plants graded 1 severe symptom of typical fruit lesions and some fruit deformation, for the plants graded 2 moderate lesions in some of the fruits only and 3 light symptoms. Only plants having 3.5 and 4, i.e. without symptoms on the fruits would be considered as resistant.

TABLE 3

Fruit evaluation of second screening

| Line | Total number of plants | Number of plants With a fruit rating of symptoms | | | | | | Conclusion |
|---|---|---|---|---|---|---|---|---|
| | | 1 | 1.5 | 2 | 2.5 | 3 | 3.5 | |
| Hazera no. 1 | 20 | 0 | 0 | 0 | 0 | 0 | 20 | Tolerant |
| Hazera no. 2 | 20 | 20 | 0 | 0 | 0 | 0 | 0 | Susceptible |
| F2 Haz1 × Haz2 | 238 | 101 | 28 | 21 | 12 | 21 | 55 | Segregating |

The phenotyping data of the F2 plants tend to demonstrate that the fruit tolerance and/or resistance to the Tomato Brown Rugose fruit virus is controled in a recessive manner by a few, one or two QTLs.

Example 4: Association Analysis for Gene Mapping

The tomato plants Hazera no. 1 and Hazera no. 2 were used to build an F2 bi-parental mapping population. The tomato plant Hazera no. 1 showing a resistant phenotype (fruit and foliar) to Tomato Brown Rugose Fruit virus was crossed with the susceptible plant in order to create an F1 which was used later to generate an F2 segregating population. Additional bi-parental population used for validation (foliar QTL) based on Hazera no. 3 and Hazera no. 4 was developed in the same manner (see example 6).

DNA Extraction : DNA was extracted from leaves ground using NucleoMag® Plant kit (Macherey-Nagel) according to the manufacturer's procedures. DNA purification was based on Magnetic-bead technology for the isolation of genomic DNA from plant tissue. DNA concentrations were quantified with a NanoDrop spectrophotometer.

The genotyping of the F2 population (based on Hazera no. 1 and Hazera no. 2) was done using a custom made Affymetrix Axium chip array containing approximatively 9500 SNPs for tomatoes (multiplex genotyping technology).

Tomatoes SNP markers were selected and discovered from different sources including public domain, LVS projects and collaborations. All SNPs were validated in pre-screen (previous experience on other technologies) and were selected according the following:

Polymorphic/ Allele frequency
Representing world wide variation
SNP clusters removal
SNPs placed evenly according to physical map distance
Lower representation in heterochromatin (pericentromeric) regions-high LD Genotyping with the Affymetrix Axiom chip array was made using the standard protocol recommended by the manufacturer. The procedure includes the following steps: DNA amplification, fragmentation, precipitation, resuspension and hybridization preparation, hybridization to chip, wash, ligation, stain and scan. Two last steps are performed by Affymetrix's GeneTitan instrument. The analysis is performed by an automatic algorithm of clustering developed by Affymetrix.

A mixed linear model association was used independently for both fruit and foliar symptoms.

The mapping results revealed one candidate QTL associated with the foliar tolerance and/or resistance to Tomato Brown rugose Fruit virus located on chromosome 11 and two candidate QTLs associated with fruit tolerance and/or resistance to Tomato Brown rugose Fruit virus located on chromosomes 6 and chromosome 9.

Markers significantly linked with the various QTLs for foliar and/or fruit tolerance/resistance to Tomato Brown rugose Fruit virus and their position on the tomato genome are summarized in Table 4. The sequence of the SNPs, including the flanking sequences are reported in table 5 and accompanying sequence listing part of the application.

Results showed that one QTL (QTL1 of the present invention) responsible for the fruit tolerance and or resistance to Tomato Brown rugose Fruit virus was located on chromosome 6, between position 33 932 438 and position 33 933 905, and that the second QTL (QTL2 of the present invention) responsible for the fruit tolerance and/or resistance to Tomato Brown rugose Fruit virus was located on chromosome 9, between position 4 800 680 and position 59 014 540, such physical positions on the genome being based on the version 2.40 of the tomato genome (Bombarely 2011). The region of chromosome 9 is a region of low recombination rate.

The region of chromosome 6 is a region prone to introgression and several genes of interest have already been mapped in this region, inter alia introgression of genes involved in salt tolerance from S. lycopersicoides, S. pennellii and S. pimpinellifolium (Li et al, Euphytica (2011) 178: 403), introgression of genes involved in powdery mildew resistance from S. habrochaites and S. neorickii (Seifi et al, Eur J Plant Pathol (2014) 138: 641) and introgression of genes involved in Pepino Mosaic Virus (WO2013/064641).

Results showed that the QTL responsible for the foliar tolerance and/or resistance to Tomato Brown rugose Fruit virus was located on chromosome 11, between position 9 548 029 and position 10 015 478, such physical position on the genome being based on the version 2.40 of the tomato genome (Bombarely 2011).

A further analysis was conducted with additional markers in order to better characterize the QTL on chromosome 11 responsible for the foliage resistance. The results are presented in table 6 and the sequences of the SNPs are reported in tables 5 and 7.

These additional results allow to define, on the basis of the p-value and $R^2$ values, and on the variation of these values along chromosome 11, that the QTL responsible for the foliar tolerance to Tomato Brown rugose Fruit virus was broadly located on chromosome 11, between the SNPs TO-0122252 and TO-0162427, i.e. between position 8 090 264 and position 10 018 811, such physical positions on the genome being based on the version 2.40 of the tomato genome. The SNPs TO-0122252 and TO-0162427 flanking the broader definition of the QTL locus are mentioned by an asterisk (*) in table 6. A narrower definition of the location of the QTL on chromosome 11 is the region defined by the SNPs TO-0142270 and TO-0162432. These flanking markers of the narrower definition of the locus are mentioned by (**) in table 6. The SNPs having the more significant association with the QTL conferring foliar resistance/tolerance are mentioned by "+" in table 6, namely TO-0181040, TO-0123057 and T060125528.

TABLE 4 list of SNPs, their position and the alleles found in susceptible plants (1st nucleotide mentioned: S allele) vs. the alleles of the markers linked to the tolerance/resistance ($2^{nd}$ nucleotide mentioned: T allele).

| SNP | $R^2$ | Pvalue | Chromosome | Position SL2.40 | S/T allele |
|---|---|---|---|---|---|
| TO-0005197 | 0.33402601 | 5.61E−08 | 6 | 33932438 | C/T |
| TO-0145581 | 0.33402601 | 5.61E−08 | 6 | 33933905 | T/C |
| TO-0180955 | 0.33863743 | 1.68E−11 | 9 | 4800680 | A/G |
| TO-0196724 | 0.351965936 | 4.96E−12 | 9 | 5203457 | T/C |
| TO-0145125 | 0.347544015 | 6.03E−12 | 9 | 40025769 | A/G |
| TO-0196109 | 0.33402601 | 2.09E−11 | 9 | 59014540 | T/G |
| TO-0182276 | | | 11 | 9548029 | A/G |
| TO-0181040 | 0.848753 | 2.35E−50 | 11 | 9797143 | A/G |
| TO-0123057 | 0.8477487 | 5.33945E−51 | 11 | 9825111 | T/G |
| TO-0125528 | 0.8477487 | 5.33945E−51 | 11 | 9837711 | G/A |
| TO-0162432 | 0.7216998 | 8.88E−34 | 11 | 10015478 | T/C |

TABLE 5 sequence of the SNPs

| | SEQ ID | Sequence of the SNPs: the allele associated with the Tomato Brown rugose Fruit virus tolerance or resistance is mentioned second in the bracket |
|---|---|---|
| TO-0005197 | 1 | GTCGGACCAAGAAACCATATTTG GTAACGGGTTCGAGTTGCTGCCT GAACCTTTTAGCCC[C/T]TTGC AATATTTGTGAAGTGATATTCCT TTGTGTTATTAATAATTTTTCGT TTTGAGTTTT |
| TO-0145581 | 2 | TTCAGAGAGCAACACTCCTGCAA GACCAACTCGGAGTAATTCAGTA ACTCGACCTTCCAT[T/C]TCTA GCTCTCAGTATAGTACTTACTCA |

TABLE 5-continued sequence of the SNPs

| SEQ ID | Sequence of the SNPs: the allele associated with the Tomato Brown rugose Fruit virus tolerance or resistance is mentioned second in the bracket |
|---|---|
| | AATAAATCAGGCTCTATTCTAAA CACAAGCTCT |
| TO-0180955 3 | TTCCGAAATGAGGACGATCCATC AGCTTCTTCAGCTGAGAGCCCCT GGTC[A/G]ACATACCAGAATTC TGTTTTTCTAAAACTGTCCAAAA TCTCCTGTAAAGA |
| TO-0196724 4 | GATTTGAATGCCTTGCCACAGCC AGAGGATGACGA[T/C]GAGATT TTTGGACAACAATTAGAAGATGA ACCACA |
| TO-0145125 5 | AGAGAATGATATCACTGCCTTAG TTTCTCAATTAAAAGTTGTGCAA AAACAAAACACACA[A/G]CTAG ATGAAGAAAACAGAGCATTCGCC TCAAAGCTTCAGACAAAAGAAGT TGAGAACAAC |
| TO-0196109 6 | TACAATACCTTCTGGCATCCCTT TCCGCAAAACGA[T/G]AGATCT TTAGTATCAAAACCGAGAGCACT GTCACC |
| TO-0182276 13 | CTCCTATTGAACATCCTGAAAAC TTGTGTCTACATCATGAGAAGAT GCAGGCCAATTC[A/G]CTCAGT ACATGGAATGCACGAGCATGTTA |

TABLE 5-continued sequence of the SNPs

| SEQ ID | Sequence of the SNPs: the allele associated with the Tomato Brown rugose Fruit virus tolerance or resistance is mentioned second in the bracket |
|---|---|
| | GGGGAATTCTAACGCAAAGCATA AGCTTGATACTTGAATAAAAGAT GAAACATACTTACTTCTTCTCAA ACT |
| TO-0181040 14 | CTCTTGGTGACAAACCACTGGCT CAATTTCTTCGCGAAGCTAAAGC TATC[A/G]CTGATGAGCTTGTC ACGGCAGGCACACGTGTCTCCTG ATGAATTCAATGC |
| TO-0123057 15 | CATTACTGTTGAGATATCTCATC GGCAACCCCTGGAGCTTGCCCAC CCGC[T/G]TGTCCTCCAGGATC TGATTTCAGAAAGGATGAATAGT AACTGTGTTTCAG |
| TO-0125528 16 | CAAGAACCCAACGACTTCTTCTT CTTTGCTTATTGAAAAACTTGGT TTTGAAATGAAAGG[G/A]ATCG AGAAATTGGATACTCAGTGGTTC TCTACTACTAAACCTTCTCCTGA TTTTAAGAAA |
| TO-0162432 17 | TGATCGACAATTCTTGTTGTTGT TGAAACTCTGCAAGTGAGAGAGG GATG[T/C]ATATAGAGAAAGGA TATTGGTAAAGGACAATTCTAGA AGGGTCTAGGGAA |

TABLE 6 additional flanking markers - association analysis mapping foliage resistance based on F2 population of HAZ1. The alleles found in susceptible plants (S allele) and the alleles of the markers linked to the tolerance/resistance (2$^{nd}$ nucleotide mentioned: T allele) are reported.

| SNP | $R^2$ | Pvalue | Position on chromosome 11 SL2.40 | Flanking markers | S/T allele |
|---|---|---|---|---|---|
| TO-0122252 | 0.7758002 | 1.16E-40 | 8090264 | * | A/T |
| TO-0144325 | 0.8101493 | 9.62E-45 | 8140310 | | |
| TO-0144322 | 0.8001583 | 1.10E-42 | 8163278 | | |
| TO-0144317 | 0.8051598 | 2.07E-44 | 8334467 | | |
| TO-0101684 | 0.8051598 | 2.07E-44 | 8345699 | | |
| TO-0197358 | 0.8051598 | 2.07E-44 | 8357644 | | |
| TO-0144313 | 0.8051598 | 2.07E-44 | 8410749 | | |
| TO-0144309 | 0.8249175 | 1.65E-46 | 8412924 | | |
| TO-0144308 | 0.8051598 | 2.07E-44 | 8414574 | | |
| TO-0144303 | 0.8051598 | 2.07E-44 | 8419932 | | |
| TO-0121816 | 0.797688 | 2.30E-42 | 8626324 | | |
| TO-0142268 | 0.7613548 | 5.39E-39 | 8631287 | | |
| TO-0142270 | 0.8064465 | 1.37E-44 | 8633469 | ** | C/T |
| TO-0142294 | 0.8474345 | 6.06E-51 | 8764030 | | |
| TO-0142299 | 0.8474345 | 6.06E-51 | 8891489 | | |
| TO-0142301 | 0.8474345 | 6.06E-51 | 8000707 | | |
| TO-0142302 | 0.8474345 | 6.06E-51 | 8902922 | | |
| TO-0142303 | 0.8474345 | 6.06E-51 | 8903092 | | |
| TO-0142305 | 0.8474345 | 6.06E-51 | 8963512 | | |
| TO-0142306 | 0.8474345 | 6.06E-51 | 9318832 | | |
| TO-0142307 | 0.8474345 | 6.06E-51 | 9318930 | | |
| TO-0162436 | 0.7855676 | 7.54E-41 | 9789608 | | |
| TO-0181040 | 0.848753 | 2.35E-50 | 9797143 | + | A/G |
| TO-0123057 | 0.8477487 | 5.34E-51 | 9825111 | + | T/G |
| TO-0125528 | 0.8477487 | 5.34E-51 | 9837711 | + | G/A |
| TO-0162432 | 0.7216998 | 8.88E-34 | 10015478 | ** | T/C |
| TO-0162427 | 0.7459438 | 2.53E-37 | 10018811 | * | C/T |

TABLE 7 sequences of the additional SNPs

| | SEQ ID | Sequence of the SNPs; the allele associated with the TBRFV tolerance or resistance is mentioned second in the bracket |
|---|---|---|
| TO-0122252 | 7 | ATGGCAATAGTGAACTGCAGAT ACAACTGAAATTGCAGAACACC CTTAAA[A/T]ATAGAATCAAT AGAAAGTTGCAACAATATTTGA ATGATGAAGCAACAAAG |
| TO-0142270 | 9 | AACACCAGGTAGAGAGCACAGC GAAACAATGGCCTCAGGAAGAT CTACTT[C/T]GCGAAGTGCAG CAAGCCACTCCATACCTCCACC AGGCTTTGATTTCAGTG |
| TO-0162427 | 18 | GCACCAGTTATAGTAATGTCCT GCTTCTTTCCTGTACCCTTATC AGTAGC[C/T]GTGACAGAAAG AATACCGTTGGTGTCAATGTCG AACTTCACTTCAATCTG |

Example 5: Further Marker Validation

One most associated marker to foliar tolerance to TBRF virus was defined at the edge of the QTL3 region to be the candidate marker close to the resistance gene. This SNP was designed to SNP monoplex KASPar technology: KASPar assay used for validation was preformed based on KASP method from KBioscience (LGC Group, Teddington, Middlesex, UK).

Primers for the KASP SNP assays were designed using LGC's primer picker software. Due to a SNP, two allele-specific forward primers and one common reverse primer per SNP assay were designed. KASP genotyping assays are based on competitive allele-specific PCR and enable bi-allelic scoring of SNPs at specific loci. To summarize, the SNP-specific KASP assay mix and the universal KASP Master mix were added to DNA samples, a thermal cycling reaction was then performed, followed by an end-point fluorescent read. Biallelic discrimination was achieved through the competitive binding of two allele-specific forward primers, each with a unique tail sequence that corresponded with two universal FRET (fluorescence resonant energy transfer) cassettes, one of which was labelled with FAMTM dye and the other of which was labelled with VICTM dye (LGC, www.lgcgroup.com).

A volume of 3 μl of DNA was pipetted into black 384 well hard shell PCR plates and dried down at room temperature. When the genotyping was performed, the DNA was suspended by adding a 3 μl PCR mix, according to the manufacturer's protocol (KBioscience). Genotyping PCR results were analyzed using the software KlusterCaller (KBioscience). The marker used in this study is the TO-0182276 (SEQ ID NO:13).

HAZ3×HAZ4 F2 population (table 2) was used for this marker validation. The F2 plants were genotyped using this marker and also phenotyped for foliar symptoms as described in example 3. The association was 100% based on a data of 251 plants.

The summary data of phenotyping foliar symptoms and candidate marker genotyping is presented in table 8: R marker means homozygous to resistance/tolerance allele, S marker means homozygous to susceptible allele, H marker means heterozygous comprising of the two alleles:

TABLE 8

| | Number of plants | Number of plants with foliar TBRFV tolerance or resistance symptoms | Number of plants with foliar TBRFV susceptibility symptoms |
|---|---|---|---|
| R marker | 67 | 67 | 0 |
| S marker | 62 | 0 | 62 |
| H marker | 122 | 0 | 122 |

Example 6: Association Analysis for Gene Mapping

The tomato plants Hazera no. 3 and Hazera no. 4 were used to build an F2 bi-parental mapping population. The tomato plant Hazera no. 3 showing a foliar resistance phenotype to Tomato Brown Rugose Fruit virus was crossed with the susceptible plant Hazera no. 4 in order to create an F1 which was used later to generate an F2 segregating population.

Crosses, phenotyping and associations were performed as described in example 4, with HAZ1 and HAZ2.

The QTL for foliar resistance and the most significant associated markers were identified on chromosome 11, as detailed in table 9 and illustrated on FIG. 3.

As in example 4, the broader definition of the locus comprising the QTL is defined by flanking markers with an asterisk in table 9, namely SNPs TO-012252 and TO0162427. These SNPs are the same as those flanking the broader definition of the QTL position as deduced from the results obtained with the other tolerance source, namely HAZ1. This point strongly corroborates the conclusion that the QTL for foliar tolerance is the same for HAZ1 and HAZ3.

HAZ1 corresponds to the seeds HAZTBRFVRES1 deposited at the NICMB under the accession number 42758.

A narrower definition of the locus of the QTL, as deduced from the results on HAZ3 population is defined by the flanking makers TO-0144317 and TO-0125528 on chromosome 11 (markers ** in table 9). The markers with the most significant association to TBRFV foliar tolerance/resistance are the markers mentioned with (+), namely TO-0142303, TO-0142306 and TO60142294.

TABLE 9 list of additional SNPs, their position and the alleles found in susceptible plants (1st nucleotide mentioned: S allele) vs. the alleles of the markers linked to the tolerance/resistance (2$^{nd}$ nucleotide mentioned: T allele)

| SNP | $R^2$ | Pvalue | Position on chromosome 11 SL2.40 | Flanking markers | S/T allele |
|---|---|---|---|---|---|
| TO-0122252 | 0.81927235 | 1.55E−60 | 8090264 | * | A/T |
| TO-0144317 | 0.854230073 | 6.90E−69 | 8334467 | ** | T/C |
| TO-0142303 | 0.884698061 | 3.46E−77 | 8903092 | + | C/A |
| TO-0142305 | 0.884698061 | 3.46E−77 | 8963512 | | |
| TO-0142306 | 0.884698061 | 3.46E−77 | 9318832 | + | G/A |
| TO-0142307 | 0.884698061 | 3.46E−77 | 9318930 | | |
| TO-0142294 | 0.884698061 | 3.46E−77 | 8764030 | + | A/G |
| TO-0142299 | 0.884698061 | 3.46E−77 | 8891489 | | |
| TO-0142301 | 0.884698061 | 3.46E−77 | 8900707 | | |
| TO-042302 | 0.884698061 | 3.46E−77 | 890292 | | |
| TO-0144308 | 0.854199247 | 7.02E−69 | 8414574 | | |
| TO-0144303 | 0.854199247 | 7.02E−69 | 8419932 | | |
| TO-0142268 | 0.854144413 | 7.24E−69 | 8631287 | | |
| TO-0142270 | 0.854144413 | 7.24E−69 | 8633469 | | |
| TO-0121816 | 0.854144413 | 7.24E−69 | 8626324 | | |
| TO-0144313 | 0.853890923 | 2.18E−68 | 8410749 | | |
| TO-0181040 | 0.851931696 | 2.47E−68 | 9797143 | | |
| TO-0123057 | 0.851931696 | 2.47E−68 | 9825111 | | |
| TO-0125528 | 0.851931696 | 2.47E−68 | 9837711 | ** | G/A |
| TO-0144309 | 0.853578274 | 6.78E−68 | 8412924 | | |
| TO-0162436 | 0.851618235 | 7.62E−68 | 9789608 | | |
| TO-0197358 | 0.848638959 | 9.80E−67 | 8357644 | | |
| TO-0101684 | 0.831991299 | 7.32E−64 | 8345699 | | |
| TO-0144325 | 0.821665121 | 9.46E−62 | 8140310 | | |
| TO-0144322 | 0.822371998 | 1.62E−61 | 8163278 | | |
| TO-0162427 | 0.789778057 | 6.28E−56 | 10018811 | * | C/T |

TABLE 10 sequence of the additional SNPs

| SNP | SEQ ID | Sequence of the SNPs; the allele associated with the TBRFV tolerance or resistance is mentioned second in the bracket |
|---|---|---|
| TO-0144317 | 8 | AGCCATTGTGATTGTGTCTGTT GTACATTACCAAAATTCTCTAG AGAAAG[T/C]GATACACATGC CAGCCCTATCGATATAAAGCAA CGCAAGGTGGATTCTGC |
| TO-0142303 | 11 | GAGGAGCTATCAACTTCATAGT CAGATTCAGAAAATGATTCAGA TGAGGA[C/A]GTGGCTGATTC TTCTTGTTTTCTTTTCTTCCTT CTGCTCGAACTCTCTCC |
| TO-0142306 | 12 | CAGAAATAATAGAAAATCAGAA AGAAAAATCAGCTTTCTAAATG GAAAAG[G/A]CGATGGCACTA TGTTTGAAGTTTTAAGCAACTT TTCTGAAGTCCCAAAAG |
| TO-0142294 | 10 | TCAACTGCAACTTTAACAGCTG ATTCAACTTCTTCTTCTTTCGA AACATC[A/G]CATTGAATGTA ACGACCTCCAATAGATTCAGCT AAACTTGTACCTACTTC |

Taken together, these results confirm the presence of a QTL conferring foliar tolerance, broadly located within the chromosomal region delimited by TO-012252 and TO0162427 and more precisely by TO-0144317 and TO-0125528.

In view of the results of example 4, these results thus demonstrate that the location of this QTL can advantageously been defined as between TO-0142270 and TO-0125528.

Example 7: Genetic Modification of Tomato Seeds by Ethyl Methane Sulfonate (EMS)

Seeds of a tomato varieties are to be treated with EMS by submergence of approximately 2000 seeds per variety into an aerated solution of either 0.5% (w/v) or 0.7% EMS for 24 hours at room temperature.

Approximately 1500 treated seeds per variety per EMS dose are germinated and the resulting plants are grown, preferably in a greenhouse, for example, from May to September, to produce seeds.

Following maturation, M2 seeds are harvested and bulked in one pool per variety per treatment. The resulting pools of M2 seeds are used as starting material to identify the individual M2 seeds and the plants with a fruit and/or a foliar tolerance to Tomato Brown Rugose Fruit virus.

What is claimed is:

1. A Solanum lycopersicum plant comprising homozygously in its genome the following three quantitative trait loci:
   a) QTL3, on chromosome 11, that confers to the plant an improved phenotype corresponding to foliar tolerance to Tomato Brown Rugose Fruit virus,
   b) QTL1, on chromosome 6, that confers to the plant an improved phenotype corresponding to fruit tolerance to Tomato Brown Rugose Fruit virus, and
   c) QTL2, on chromosome 9, that that confers to the plant an improved phenotype corresponding to fruit tolerance to Tomato Brown Rugose Fruit virus;

and wherein said QTLs are present in the genome of a plant, seeds of which designated HAZTBRFVRES1 have been deposited with NCIMB under accession number 42758.

2. A *S. lycopersicum* plant according to claim 1, wherein said QTLs are to be found, for QTL1, on chromosome 6, within the chromosomal region delimited by TO-0005197 (SEQ ID NO:1) and TO-015581 (SEQ ID NO:2), for QTL2, on chromosome 9, within the chromosomal region delimited by TO-0180955 (SEQ ID NO:3) and TO-0196109 (SEQ ID NO:6) and for QTL3, on chromosome 11, within the chromosomal region delimited by TO-0122252 (SEQ ID NO:7) and TO-0162427 (SEQ ID NO:18).

3. A *S. lycopersicum* plant according to claim 1, wherein said QTLs are to be found at one or more of the following loci:
   a) locus encompassing TO-0005197 (SEQ ID NO:1) on chromosome 6
   b) locus encompassing TO-0145581 (SEQ ID NO:2) on chromosome 6
   c) locus encompassing TO-0180955 (SEQ ID NO:3) on chromosome 9
   d) locus encompassing TO-0196724 (SEQ ID NO:4) on chromosome 9
   e) locus encompassing TO-0145125 (SEQ ID NO:5) on chromosome 9
   f) locus encompassing TO-0196109 (SEQ ID NO:6) on chromosome 9
   g) locus encompassing TO-0122252 (SEQ ID NO:7) on chromosome 11,
   h) locus encompassing TO-0144317 (SEQ ID NO:8) on chromosome 11,
   i) locus encompassing TO-0142270 (SEQ ID NO:9) on chromosome 11;
   j) locus encompassing TO-0142294 (SEQ ID NO:10) on chromosome 11,
   k) locus encompassing TO-0142303 (SEQ ID NO:11) on chromosome 11,
   l) locus encompassing TO-0142306 (SEQ ID NO:12) on chromosome 11,
   m) locus encompassing TO-0182276 (SEQ ID NO:13) on chromosome 11,
   n) locus encompassing TO-0181040 (SEQ ID NO:14) on chromosome 11,
   o) locus encompassing TO-0123057 (SEQ ID NO:15) on chromosome 11
   p) locus encompassing TO-0125528 (SEQ ID NO:16) on chromosome 11,
   q) locus encompassing TO-0162432 (SEQ ID NO:17) on chromosome 11, and
   r) locus encompassing TO-0162427 (SEQ ID NO:18) on chromosome 11.

4. The *S. lycopersicum* plant according to claim 1, characterized by the presence in the genome of said *S. lycopersicum* plant of at least one of the following alleles associated with each of QTL1, QTL2, and QTL3:
   a) allele T of TO-0005197, or
   b) allele C of TO-0145581 for QTL1; and
   c) allele G of TO-0180955,
   d) allele C of TO-0196724,
   e) allele G of TO-0145125, or
   f) allele G of TO-0196109 for QTL2; and
   g) allele T of TO-0122252,
   h) allele C of TO-0144317,
   i) allele T of TO-0142270,
   j) allele G of TO-0142294,
   k) allele A of TO-0142303,
   l) allele A of TO-0142306,
   m) allele G of TO-0182276,
   n) allele G of TO-0181040,
   o) allele G of TO-0123057,
   p) allele A of TO-0125528,
   q) allele C of TO-0162432, or
   r) allele T of TO-0162427 for QTL3.

5. The plant according to claim 1, wherein said plant is a progeny of seeds of HAZTBRFVRES1 (NCIMB accession number 42758).

6. A cell of a *S. lycopersicum* plant according to claim 1, comprising in its genome said QTL1 on chromosome 6, said QTL2 on chromosome 9 and said QTL3 on chromosome 11, conferring the improved phenotype corresponding to fruit and foliar tolerance to TBRF virus.

7. A plant part of a *S. lycopersicum* plant according to claim 1 selected from the group consisting of seeds, explants, reproductive material, scion, cutting, seed, fruit, root, rootstock, pollen, ovule, embryo, protoplast, leaf, anther, stem, petiole or flowers, wherein said plant part comprises cells of a *S. lycopersicum* plant comprising in its genome QTL1 on chromosome 6, QTL2 on chromosome 9 and QTL3 on chromosome 11, conferring the improved phenotype corresponding to fruit and foliar tolerance to TBRF virus.

8. A seed of a *S. lycopersicum* plant, which develops into a plant according to claim 1.

9. A tissue culture of regenerable cells of the plant according to claim 1 wherein the regenerable cells are derived from embryos, protoplasts, meristematic cells, callus, pollen, leaves, anthers, stems, petioles, roots, root tips, seeds, flowers, cotyledons, and/or hypocotyls, and contain in their genome said QTL1 on chromosome 6, said QTL2 on chromosome 9 and said QTL3 on chromosome 11 conferring the improved phenotype corresponding to fruit and foliar tolerance to TBRF virus.

10. A method for detecting *S. lycopersicum* plants according to claim 1 having foliar tolerance to Tomato Brown Rugose Fruit virus, said method comprising detecting at least one of the following markers allele T of TO-0122252, allele C of TO-0144317, allele T of TO-0142270, allele G of TO-0142294, allele A of TO-0142303, allele A of TO-0142306, allele G of TO-0182276, allele G of TO-0181040, allele G of TO-0123057, allele A of TO-0125528, allele C of TO-0162432 and allele T of TO-0162427 in a genetic material sample of the plant.

11. A method for breeding *S. lycopersicum* plants having tolerance to TBRFV, comprising the steps of crossing a plant grown from the deposited seeds NCIMB 42758 or progeny thereof bearing QTL1, QTL2 and QTL3 conferring TBRFV tolerance, with an initial *S. lycopersicum* plant devoid of said QTLs.

12. The method of claim 11, comprising the steps of:
   a) crossing a plant grown from the deposited seeds NCIMB 42758, or progeny thereof, bearing QTL1, QTL2 and QTL3 conferring TBRFV tolerance, and an initial *S. lycopersicum* plant devoid of said QTLs,
   b) selecting a plant in the progeny thus obtained, bearing QTL1, QTL2 and QTL3; and
   c) optionally self-pollinating one or several times the plant obtained in step b) and selecting from the progeny thus obtained a plant having tolerance to TBRFV.

13. The method of claim 11, comprising the steps of:
   a1) crossing a plant grown from the deposited seeds NCIMB 42758 or progeny thereof, bearing QTL1, QTL2 and QTL3 conferring TBRFV tolerance, and an initial *S. lycopersicum* plant, devoid of said QTLs, thus generating an F1 population,
   a2) selfing the F1 hybrids to create an F2 population, and
   b) selecting individuals from the progeny thus obtained having tolerance to TBRFV.

14. The method of claim 12, wherein SNPs markers are used in steps b) and/or c) for selecting plants bearing QTL1, QTL2 and QTL3 conferring TBRFV tolerance.

15. The method according to claim 12, wherein the selection is carried out by detecting at least one of the following alleles: allele T of TO-0005197, allele C of TO-0145581, allele G of TO-0180955, allele C of TO-0196724, allele G of TO-0145125, allele G of TO-0196109, allele T of TO-0122252, allele C of TO-0144317, allele T of TO-0142270, allele G of TO-0142294, allele A of TO-0142303, allele A of TO-0142306, allele G of TO-0182276, allele G of TO-0181040, allele G of TO-0123057, allele A of TO-0125528, allele C of TO-0162432 and allele T of TO-0162427.

16. A *S. lycopersicum* plant obtained by the method according to claim 15, wherein said plant comprises QTL1, QTL2 and QTL3 conferring TBRFV tolerance.

* * * * *

SEQUENCE LISTING

<160> NUMBER OF SEQ ID NOS: 18

<210> SEQ ID NO 1
<211> LENGTH: 121
<212> TYPE: DNA
<213> ORGANISM: Lycopersicon esculentum
<220> FEATURE:
<221> NAME/KEY: polymorphism
<222> LOCATION: (61)..(61)
<223> OTHER INFORMATION: susceptible = C; tolerant = T

<400> SEQUENCE: 1
gtcggaccaa gaaaccatat ttggtaacgg gttcgagttg ctgcctgaac cttttagccc      60
yttgcaatat ttgtgaagtg atattccttt gtgttattaa taatttttcg ttttgagttt     120
t                                                                     121

<210> SEQ ID NO 2
<211> LENGTH: 121
<212> TYPE: DNA
<213> ORGANISM: Lycopersicon esculentum
<220> FEATURE:
<221> NAME/KEY: polymorphism
<222> LOCATION: (61)..(61)
<223> OTHER INFORMATION: susceptible = T; tolerant = C

<400> SEQUENCE: 2
ttcagagagc aacactcctg caagaccaac tcggagtaat tcagtaactc gaccttccat      60
ytctagctct cagtatagta cttactcaaa taaatcaggc tctattctaa acacaagctc     120
t                                                                     121

<210> SEQ ID NO 3
<211> LENGTH: 101
<212> TYPE: DNA
<213> ORGANISM: Lycopersicon esculentum
<220> FEATURE:
<221> NAME/KEY: polymorphism
<222> LOCATION: (51)..(51)
<223> OTHER INFORMATION: susceptible = A; tolerant = G

<400> SEQUENCE: 3
ttccgaaatg aggacgatcc atcagcttct tcagctgaga gccctggtc racataccag       60 aattctgttt ttctaaaact gtccaaaatc tcctgtaaag a                         101

<210> SEQ ID NO 4
<211> LENGTH: 71
<212> TYPE: DNA
<213> ORGANISM: Lycopersicon esculentum
<220> FEATURE:
<221> NAME/KEY: polymorphism
<222> LOCATION: (36)..(36)
<223> OTHER INFORMATION: susceptible = T; tolerant = C

<400> SEQUENCE: 4
gatttgaatg ccttgccaca gccagaggat gacgaygaga ttttggaca acaattagaa       60 gatgaaccac a                                                           71

<210> SEQ ID NO 5
<211> LENGTH: 121
<212> TYPE: DNA
<213> ORGANISM: Lycopersicon esculentum
<220> FEATURE:
<221> NAME/KEY: polymorphism
<222> LOCATION: (61)..(61)
<223> OTHER INFORMATION: susceptible = A; tolerant = G -continued

```
<400> SEQUENCE: 5
agagaatgat atcactgcct tagtttctca attaaaagtt gtgcaaaaac aaaacacaca        60
rctagatgaa gaaaacagag cattcgcctc aaagcttcag acaaagaag ttgagaacaa        120 c                                                                      121

<210> SEQ ID NO 6
<211> LENGTH: 71
<212> TYPE: DNA
<213> ORGANISM: Lycopersicon esculentum
<220> FEATURE:
<221> NAME/KEY: polymorphism
<222> LOCATION: (36)..(36)
<223> OTHER INFORMATION: susceptible = T; tolerant = G

<400> SEQUENCE: 6 tacaataacct tctggcatcc ctttccgcaa aacgakagat ctttagtatc aaaaccgaga       60
gcactgtcac c                                                            71

<210> SEQ ID NO 7
<211> LENGTH: 101
<212> TYPE: DNA
<213> ORGANISM: Lycopersicon esculentum
<220> FEATURE:
<221> NAME/KEY: polymorphism
<222> LOCATION: (51)..(51)
<223> OTHER INFORMATION: susceptible = A; tolerant = T

<400> SEQUENCE: 7
atggcaatag tgaactgcag atacaactga aattgcagaa cacccttaaa watagaatca       60
atagaaagtt gcaacaatat ttgaatgatg aagcaacaaa g                          101

<210> SEQ ID NO 8
<211> LENGTH: 101
<212> TYPE: DNA
<213> ORGANISM: Lycopersicon esculentum
<220> FEATURE:
<221> NAME/KEY: polymorphism
<222> LOCATION: (51)..(51)
<223> OTHER INFORMATION: susceptible = T; tolerant = C

<400> SEQUENCE: 8
agccattgtg attgtgtctg ttgtacatta ccaaaattct ctagagaaag ygatacacat       60
gccagcccta tcgatataaa gcaacgcaag gtggattctg c                          101

<210> SEQ ID NO 9
<211> LENGTH: 101
<212> TYPE: DNA
<213> ORGANISM: Lycopersicon esculentum
<220> FEATURE:
<221> NAME/KEY: polymorphism
<222> LOCATION: (51)..(51)
<223> OTHER INFORMATION: susceptible = C; tolerant = T

<400> SEQUENCE: 9
aacaccaggt agagagcaca gcgaaacaat ggcctcagga agatctactt ygcgaagtgc       60
agcaagccac tccatacctc caccaggctt tgatttcagt g                          101

<210> SEQ ID NO 10
<211> LENGTH: 101
<212> TYPE: DNA
<213> ORGANISM: Lycopersicon esculentum
<220> FEATURE:
```

```
<221> NAME/KEY: polymorphism
<222> LOCATION: (51)..(51)
<223> OTHER INFORMATION: susceptible = A; tolerant = G

<400> SEQUENCE: 10
tcaactgcaa ctttaacagc tgattcaact tcttcttcct tcgaaacatc rcattgaatg      60
taacgacctc caatagattc agctaaactt gtacctactt c                         101

<210> SEQ ID NO 11
<211> LENGTH: 101
<212> TYPE: DNA
<213> ORGANISM: Lycopersicon esculentum
<220> FEATURE:
<221> NAME/KEY: polymorphism
<222> LOCATION: (51)..(51)
<223> OTHER INFORMATION: susceptible = C; tolerant = A

<400> SEQUENCE: 11
gaggagctat caacttcata gtcagattca gaaaatgatt cagatgagga mgtggctgat      60
tcttcttgtt ttcttttctt ccttctgctc gaactctctc c                         101

<210> SEQ ID NO 12
<211> LENGTH: 101
<212> TYPE: DNA
<213> ORGANISM: Lycopersicon esculentum
<220> FEATURE:
<221> NAME/KEY: polymorphism
<222> LOCATION: (51)..(51)
<223> OTHER INFORMATION: susceptible = G; tolerant = A

<400> SEQUENCE: 12 cagaataat agaaaatcag aagaaaaat cagctttcta aatggaaaag rcgatggcac      60
tatgtttgaa gttttaagca acttttctga agtcccaaaa g                         101

<210> SEQ ID NO 13
<211> LENGTH: 160
<212> TYPE: DNA
<213> ORGANISM: Lycopersicon esculentum
<220> FEATURE:
<221> NAME/KEY: polymorphism
<222> LOCATION: (59)..(59)
<223> OTHER INFORMATION: susceptible = A; tolerant = G

<400> SEQUENCE: 13
ctcctattga acatcctgaa aacttgtgtc tacatcatga gaagatgcag gccaattcrc      60
tcagtacatg gaatgcacga gcatgttagg ggaattctaa cgcaaagcat aagcttgata     120
cttgaataaa agatgaaaca tacttacttc ttctcaaact                          160

<210> SEQ ID NO 14
<211> LENGTH: 101
<212> TYPE: DNA
<213> ORGANISM: Lycopersicon esculentum
<220> FEATURE:
<221> NAME/KEY: polymorphism
<222> LOCATION: (51)..(51)
<223> OTHER INFORMATION: susceptible = A; tolerant = G

<400> SEQUENCE: 14
ctcttggtga caaaccactg gctcaatttc ttcgcgaagc taaagctatc rctgatgagc      60
ttgtcacggc aggcacacgt gtctcctgat gaattcaatg c                         101

<210> SEQ ID NO 15
<211> LENGTH: 101
```

```
<212> TYPE: DNA
<213> ORGANISM: Lycopersicon esculentum
<220> FEATURE:
<221> NAME/KEY: polymorphism
<222> LOCATION: (51)..(51)
<223> OTHER INFORMATION: susceptible = T; tolerant = G

<400> SEQUENCE: 15
cattactgtt gagatatctc atcggcaacc cctggagctt gcccacccgc ktgtcctcca      60
ggatctgatt tcagaaagga tgaatagtaa ctgtgtttca g                        101

<210> SEQ ID NO 16
<211> LENGTH: 121
<212> TYPE: DNA
<213> ORGANISM: Lycopersicon esculentum
<220> FEATURE:
<221> NAME/KEY: polymorphism
<222> LOCATION: (61)..(61)
<223> OTHER INFORMATION: susceptible = G; tolerant = A

<400> SEQUENCE: 16
caagaaccca acgacttctt cttctttgct tattgaaaaa cttggttttg aaatgaaagg      60
ratcgagaaa ttggatactc agtggttctc tactactaaa ccttctcctg attttaagaa    120
a                                                                    121

<210> SEQ ID NO 17
<211> LENGTH: 101
<212> TYPE: DNA
<213> ORGANISM: Lycopersicon esculentum
<220> FEATURE:
<221> NAME/KEY: polymorphism
<222> LOCATION: (51)..(51)
<223> OTHER INFORMATION: susceptible = T; tolerant = C

<400> SEQUENCE: 17
tgatcgacaa ttcttgttgt tgttgaaact ctgcaagtga gagagggatg yatatagaga     60
aaggatattg gtaaaggaca attctagaag ggtctaggga a                        101

<210> SEQ ID NO 18
<211> LENGTH: 101
<212> TYPE: DNA
<213> ORGANISM: Lycopersicon esculentum
<220> FEATURE:
<221> NAME/KEY: polymorphism
<222> LOCATION: (51)..(51)
<223> OTHER INFORMATION: susceptible = C; tolerant = T

<400> SEQUENCE: 18
gcaccagtta tagtaatgtc ctgcttcttt cctgtaccct tatcagtagc ygtgacagaa     60
agaataccgt tggtgtcaat gtcgaacttc acttcaatct g                        101
```